United States Patent
De Mooij

(10) Patent No.: US 9,808,648 B2
(45) Date of Patent: Nov. 7, 2017

(54) DEVICE, SYSTEM AND METHOD FOR IMMOBILIZATION OF A HUMAN'S BODY PART

(71) Applicant: DYNAMIC SYSTEMS HOLDING BV, Moordrecht (NL)

(72) Inventor: Leendert Gerrit De Mooij, Alicante (ES)

(73) Assignee: DYNAMIC SYSTEMS HOLDING BV, Moordrecht (NL)

(*) Notice: Subject to any disclaimer, the term of this patent is extended or adjusted under 35 U.S.C. 154(b) by 227 days.

(21) Appl. No.: 14/386,500

(22) PCT Filed: May 8, 2013

(86) PCT No.: PCT/EP2013/059644
§ 371 (c)(1),
(2) Date: Sep. 19, 2014

(87) PCT Pub. No.: WO2013/167689
PCT Pub. Date: Nov. 14, 2013

(65) Prior Publication Data
US 2015/0047652 A1 Feb. 19, 2015

(30) Foreign Application Priority Data
May 8, 2012 (NL) .................................. 1039586

(51) Int. Cl.
*A61N 5/10* (2006.01)
*A61B 6/04* (2006.01)
(Continued)

(52) U.S. Cl.
CPC .............. *A61N 5/10* (2013.01); *A61B 6/0428* (2013.01); *A61B 2090/101* (2016.02);
(Continued)

(58) Field of Classification Search
CPC ............ A61G 13/1245; A61G 13/1235; A61G 13/121; A61G 13/12; A61G 2200/325;
(Continued)

(56) References Cited

U.S. PATENT DOCUMENTS 5,531,229 A † 7/1996 Dean
5,566,681 A * 10/1996 Manwaring ............ A61G 13/12
128/845

(Continued)

FOREIGN PATENT DOCUMENTS

EP 1095640 A1 5/2001

OTHER PUBLICATIONS

Aquaplast, "Immobilization Systems for Radiation Therapy," Aquaplast Corporation, Wyckoff, New Jersey (Dec. 1989).

(Continued)

*Primary Examiner* — Ophelia A Hawthorne
(74) *Attorney, Agent, or Firm* — Knobbe, Martens, Olson & Bear LLP

(57) ABSTRACT

A system for immobilization of a patient body part for radiotherapy applications includes a device having at least one flanged support member which is mounted to a fixation surface. The device can receive and retain at least two sheets. A first sheet covers the anatomical contours of a first area of a body part. A second sheet covers the anatomical contours of a second area of the body part which is not covered by the first sheet. The system supports the immobilized body part free from the fixation surface by the two sheets and the device.

10 Claims, 36 Drawing Sheets

(51) Int. Cl.
*A61F 5/37* (2006.01)
*A61B 90/10* (2016.01)

(52) U.S. Cl.
CPC ..... *A61F 5/3769* (2013.01); *A61N 2005/1094* (2013.01); *A61N 2005/1097* (2013.01)

(58) Field of Classification Search
CPC ....... A61G 7/072; A47C 15/008; E05B 75/00; A61F 5/055; A61F 5/3723; A61F 5/3715; A61F 5/3776; A61B 90/14; A61B 90/17; A61B 90/18; A61B 2090/363; A61B 34/10; A61B 90/39; A61N 2005/1097
See application file for complete search history.

(56) References Cited

U.S. PATENT DOCUMENTS

| | | | | |
|---|---|---|---|---|
| 5,702,406 | A | * | 12/1997 | Vilsmeier ............. A61B 90/14 128/845 |
| 5,730,745 | A | | 3/1998 | Schulte et al. |
| 5,775,337 | A | * | 7/1998 | Hauger ................ A61B 6/0421 128/869 |
| 6,698,045 | B1 | † | 3/2004 | Coppens |

OTHER PUBLICATIONS

Dan Goebel, Welcome, Great Lakes TECGazette, Summer 2003, p. 1-3.†
Claton Korver, EncompassTM, Tec Times, vol. 8 issue 1, p. 5, Spring 2003.†

\* cited by examiner
† cited by third party

DEVICE, SYSTEM AND METHOD FOR IMMOBILIZATION OF A HUMAN'S BODY PART

CROSS-REFERENCE TO RELATED APPLICATIONS

This application is the U.S. National Phase under 35 U.S.C. §371 of International Application PCT/EP2013/059644, filed May 8, 2013, which claims priority to NL 1039586, filed May 8, 2012.

FIELD OF THE INVENTION

The present invention pertains to a device, a system and a method for immobilizing at least part of a human's body part for receiving radiation treatment. The invention is suitable for use in the medical field, particularly for immobilization purposes in radiotherapy and cancer treatment.

BACKGROUND

The treatment of patients having cancer frequently makes use of radiation therapy wherein radiation is directed to particular sites in the patient's body. These treatments require high precision, reliable and accurate patient set-up to position and immobilize the relevant portion of the patient's body undergoing the radiation. Various devices and equipment are available for effecting such action. For example, patient couches or tables are commonly provided at the radiation machine, e.g., linear accelerator, CT machine, MRI, etc., to support the patient in a prone or supine position while the relevant portion of the patient's body is held in a fixed or immobilized condition. To that end the immobilization of the relevant portion of the patient's body is commonly achieved by various types of devices mounted on the patient couch/treatment table.

A commonly used body part (i.e. the head) restraint device is a mask that is placed over the face of the patient to hold the patient's head stationary. Such masks may be molded to conform to the contours of the patient's face to ensure maximum immobilization. The back of the patient's head and contiguous portion of the patient's neck may be supported by a cushion which itself can be pre-contoured for a specific shape or can be conformed, e.g., molded, to the shape of the back of the patient's head. The mask itself can be pre-formed to a shape that will generally conform to the contours of the patient's face, or may be molded on the patient's face to closely conform to those contours. The molding of the mask is typically conducted preceding the first treatment. After this the mask can be mounted on the head of the patient and subsequently will be fixed to the patient support table. However, the patient's head and neck will still have to be supported, such as by cushions filled with granular material, for example, or by preformed cushions. Here, too, deviations in the position of the head in relation to the preceding treatment can easily occur.

U.S. Pat. No. 5,702,406 discloses a reference system for noninvasive, stereotactic immobilization of a human head in reproducible position. The reference system comprises a head ring having a pair of support legs adapted to be positioned at opposite sides of the head of a specific patient. The reference system also comprises a mask containing a plurality of separate parts capable of assuming a given conformation. A first part is adapted to be conformed to and to cover the anatomical contours of a first area of the specific patient's head. A second part is adapted to be conformed to and to cover the anatomical contours of a second area of the specific patient's head which is not covered by the first part. The reference system further comprises means for connecting the mask parts with one another, said connection means also connecting the connected mask parts to the reference system. Another part of the reference system is a detachable support, made of plastic and used for supporting the back of the head of the patient. One of the disadvantages of this system is that the obtained mask has an open area on the cranial side and does not fully cover the head of a patient.

US 2008/078410 discloses a support assembly for the head and neck of a patient. The assembly includes a concave shaped, conformable (e.g., a resilient foamed plastic) cushion, a holder for the cushion and a conformable, curable (e.g., thermoplastic) cover sheet. The cover sheet is heated to soften it, whereupon it can be disposed over the cushion so that the patient's head and neck can be impressed into it to conform to the contour of the head and neck. The cover sheet is then cured to permanently retain its shape. A conventional conformable mask can be used to conform it to the face of the patient whose head and neck is supported on the support assembly, thereby resulting in a combination that immobilizes the head and neck.

The main disadvantage of the above described systems resides in the use of a head support such as a support cushion. The use of said support to shape a mask adapted to a patient's head for instance, results in a mask which is adapted to the pre-shaped form of the support cushion. The obtained mask is hence not fully adapted to the anatomical contours of the body part that needs to be immobilized. In addition, the rotation of said body part will be adapted to the support cushion shape and material. This provides the patient with a very low comfort level especially if the treatment time is long.

Another disadvantage related to the use of a support cushion is the incapacity of the practitioner to be in touch with the body part surface which is supported by the support cushion. Hence, the practitioner will have a limited access to the body part surface supported by the support cushion which leads to a mask which is not fully conform to the anatomical contours of the mentioned body part. In case the practitioner has access to the body part surface which is normally supported by the support cushion of the prior art, he can ensure a perfect conformity of the mask to the anatomical contours and boney reference structures of the body part that needs to be immobilized. Moreover, the contact of the practitioner with the body part of interest will provide the patient with a security and a comfort feeling.

Still another disadvantage of the immobilization systems described in the prior art is that they comprise several devices that needs to be assembled which, on one hand, represents a high workload for the practitioner and on the other hand, prolongs the time required for the making of the immobilization mask thereby providing the patient with an uncomfortable feeling. The immobilization systems described in the prior art are also very bulky and a high amount of material is required for their manufacture which leads to a non-homogeneous dose delivery and high attenuation of the radiation beam.

The aim of the present invention is to provide a solution to overcome at least part of the above mentioned disadvantages. The invention thereto aims to provide a method, a device and a system which are highly effective and easy to use and apply for the immobilization of a patient body part.

SUMMARY

The present invention provides a system for immobilization of a patient body part for radiotherapy applications comprising: —a device comprising at least one flanged support member which is suitable to be mounted to a fixation surface and is adapted to receive and retain at least two sheets, —a first sheet for covering the anatomical contours of a first area of said body part, and —a second sheet for covering the anatomical contours of a second area of said body part which is not covered by the first sheet; whereby the system is adapted for supporting the immobilized body part free from the fixation surface by the two sheets and the device.

In a preferred embodiment, the present invention provides a system for immobilization of a patient body part for radiotherapy applications comprising: —a device comprising at least one flanged support member which is suitable to be mounted to a fixation surface and is adapted to receive and retain at least two moldable thermoplastic sheets, —a first moldable thermoplastic sheet for covering the anatomical contours of a first area of said body part; and —a second moldable thermoplastic sheet for covering the anatomical contours of a second area of said body part which is not covered by the first moldable thermoplastic sheet, whereby the system is adapted for supporting the immobilized body part free from the fixation surface by the two sheets and the device.

In a preferred embodiment, the first sheet is designed to conform the anatomical contours of the first area of the body part and the second sheet is designed to conform the anatomical contours of the second area of the body part thereby forming a double shell mask enclosing said body part.

In a preferred embodiment, the system comprises at least one flanged support member fixation means for mounting the flanged support member of the device to the fixation surface at a distance from said fixation surface, thereby mounting the flanged support member substantially parallel to the fixation surface. The flanged support member can also be mounted at a distance from said fixation surface and at a desired "pre-set" angle from said surface.

In a preferred embodiment, the flanged support member is provided with a plurality of attachment means adapted to receive and retain the sheets. In a preferred embodiment, the flanged support member is provided with a plurality of attachment means adapted to receive and retain the moldable thermoplastic sheets.

In a preferred embodiment, the first and the second sheet comprise each a circumferential rim provided with a number of connection means for mounting said sheets to the flanged support member.

In a preferred embodiment, the circumferential rims of the first sheet and of the second sheet are designed to be superimposable.

In a preferred embodiment, the connection means of the circumferential rim of the sheet are positioned such as to correspond to the connection means of the circumferential rim of the second sheet and/or to the attachment means of the flanged support member of the device.

In a preferred embodiment, the system comprises at least one stabilization means suitable to be dismountably fixed to the flanged support member for optimizing the immobilization of said body part.

In a preferred embodiment, the connection means of the circumferential rim of the first thermoplastic sheet are positioned such as to correspond to the connection means of the circumferential rim of the second thermoplastic sheet and/or to the attachment means of the flanged support member of the device when the first and the second thermoplastic sheets are simultaneously attached to the flanged support member.

The present invention further provides a device for immobilization of a patient body part for radiotherapy applications comprising at least one flanged support member suitable to receive and retain two sheets, said flanged support member is suitable to be mounted to a fixation surface using support member fixation means, such as said flanged support member is mounted and at a distance from said fixation surface.

In a preferred embodiment, the flanged support member is mounted substantially parallel to the fixation surface. The flanged support member can also be mounted at a distance from said fixation surface and at a desired "pre-set" angle from said surface.

The present invention further provides a method for immobilization of a patient body part for radiotherapy applications comprising the steps of: —mounting a device comprising a flanged support member to a fixation surface; said flanged support member is adapted to receive and retain at least two sheets; —mounting a first sheet to the flanged support member; —placing the patient body part to be immobilized on said first sheet thereby covering the anatomical contours of a first area of said body part; and —mounting a second sheet to the flanged support member thereby covering the anatomical contours of a second area of said body part which is not covered by the first sheet; Wherein the method is adapted for supporting the immobilized body part free from the fixation surface by the two sheets and the device.

In a preferred embodiment, the first and the second sheets are suitable to be formed on the patient body part such as to conform the anatomical contours of said patient body part.

In a preferred embodiment, the first and the second sheets are pre-formed sheets which are conform to the anatomical contours of the patient body part.

In a preferred embodiment, the method comprises the step of scanning the body part for pre-forming the first and the second sheets.

The present invention further provides at least two moldable thermoplastic sheets for immobilization of a patient body part for radiotherapy applications, said sheets are suitable to be connected and retained by a device comprising at least one flanged support member which is suitable to be mounted to a fixation surface, whereby the sheets and the device are adapted for supporting the immobilized body part free from the fixation surface and wherein the sheets have different physical properties. Wherein large body parts are immobilized, there will be a minimal and a very small area of contact between the patient's body and the fixation surface.

In a preferred embodiment, the said sheets are suitable to be directly molded on the patient body part thereby obtaining molded sheets. In a preferred embodiment, a first molded sheet is designed to conform the anatomical contours of a first area of the body part and a second molded sheet is designed to conform the anatomical contours of a second area of the body part thereby forming a double shell mask enclosing said body part.

In a preferred embodiment, the sheets have different elasticity. In a preferred embodiment, the elasticity ratio of the sheet with the highest elasticity to the sheet with the lowest elasticity is at least 5. In a further preferred embodiment, the elasticity of the less elastic sheet is at least 50%, preferably at least 60% and is at most 80%, preferably at most 100%.

In a preferred embodiment, the thickness of the less elastic sheet is of 1.5 to 1.8 mm, preferably about 1.7 mm. The thickness of the more elastic sheet is of 1.5 to 2.5, preferably 2 to 2.4 mm, preferably about 2.3 mm. In a preferred embodiment, at least one sheet is provided with perforations.

In a preferred embodiment, the melt temperature Tm of the sheets is in the range of from 50 to 85° C., preferably from 65 to 75° C. In a preferred embodiment, the crystallization temperature Tc of the sheets is in the range of from 19 to 25° C.

The present invention provides several improvements and advantages compared to the systems and devices of the prior art. The invention does not require using a cushion or a support for the body part to be immobilized. Hence, the immobilized body part will be supported by the sheet and the device having a flanged support member. Consequently, the sheet will be exactly adapted and conform to the anatomical contours of the immobilized body part. Wherein, moldable thermoplastic sheets are used, said sheet will deform according to only and solely the patient's body part shape and anatomical contours.

The invention also provides a full freedom of anatomical contours and rotation and position of the patient's body part. This is important to avoid the critical organs (example: glandula parotis, gladula submandibularis, glandula sublingualis nervus opticus, chiasma, truncus encephali) during treatment and will also limit the materials used in the radiation beam (skin dose, attenuation and risk on damage to skin and critical non-effected organs).

The invention does not make use of a material or a support on which the immobilized body part rests, such as cushions, as described in the systems of the prior art. Consequently, the immobilized body part of the patient is, up to 360°, accessible to the practitioner and/or for radiation application. This means that the practitioner can touch and/or apply radiation to any area of the immobilized body part. This is not offered by the systems of the prior art wherein the area of the immobilized body part resting on a cushion is neither accessible to the practitioner nor to the application of radiation.

The thermoplastic sheets according to an embodiment of the present invention provide for the above described immobilization of the body part, i.e. without use of a material or a support on which the immobilized body part rests. The thermoplastic sheets further allow the immobilization of the body part without the use of reinforcement strips. Said sheets have sufficient rigidity so that additional reinforcement strips are unnecessary. In addition, the total material thickness of the thermoplastic sheets used in the present invention is relatively low, which has a positive effect on the dosimetry. The "double shell" mask obtained by the invention fully covers and encompasses the patient's body part to be immobilized. For instance, for the head, the double shell mask covers the areas corresponding to and including the frontal bone, the parietal bone and the occipital bone while in the prior art system the area corresponding to these bones is only partially covered or is not covered.

Another advantage of the present invention is the freedom of rotation of the patient's head in the XZ and the YZ plane with respect to the areas to be treated and critical organs to be kept away from the applied radiation.

Another advantage provided by the present invention relates to the amount and type of material used for the immobilization of body part. The devices and systems of the prior art are bulky, comprise several devices which have a negative impact on the dosimetric properties and which leads to a long mounting time and discomfort for the patient. The present invention provides a system, device and a method wherein a limited amount of material and devices are used. The method, system and device according to the invention are simple to use which reduces the time and/or effort required for the production of the immobilisation device (or the double shell mask).

DESCRIPTION OF THE FIGURES

The invention will be further described in detail with reference to the exemplary embodiments represented by the accompanying figures, in which

FIG. 13 is a side view of the devices represented in FIG. 12.

DETAILED DESCRIPTION OF THE INVENTION

Figure 1:
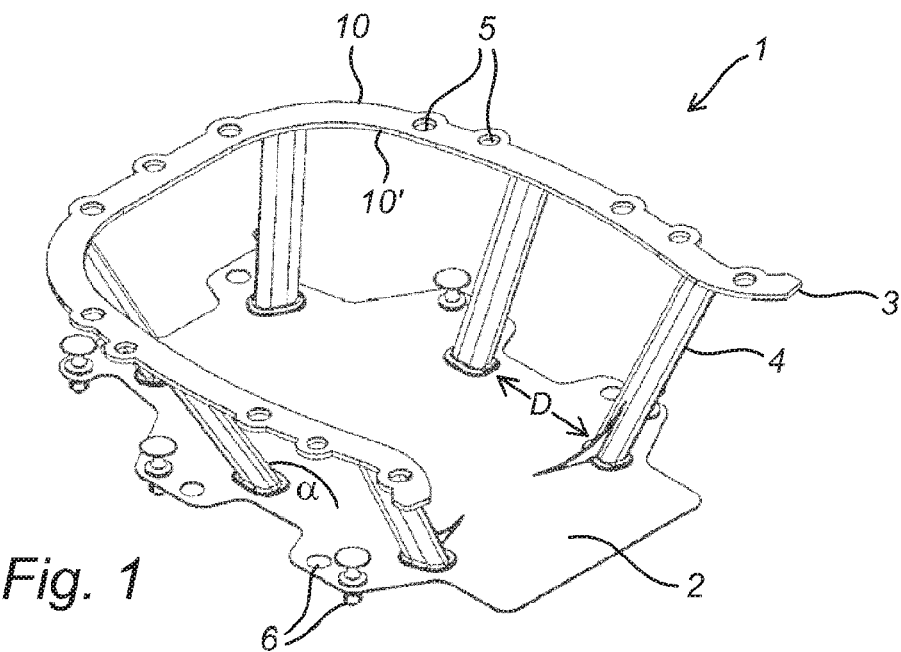
FIG. 1 shows the device according to the present invention.

The present invention relates to a method, a device and a system for the immobilization of a patient body part. The present invention can be used for the immobilization of any single body part of a human being. The present invention can also be used for the immobilization of more than one body part of a human being, such as the head, the neck and the shoulders and optionally part of the trunk. The present invention is preferably used for the immobilization of a body part for radiotherapy applications. The body part can be the part enclosing any organ of the patient such as the liver, the lungs or the kidneys, such as to deliver radiation to said organ.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The term "initial state" of a thermoplastic sheet used herein refers to a thermoplastic sheet which is still flat and not yet deformed. The term "final state" of a thermoplastic sheet used herein refers to a thermoplastic sheet which has been deformed to conform the anatomical contours of a body portion and cured thereby having a rigid molded thermoplastic sheet.

The term "cured" used herein refers to a thermoplastic sheet that was heated, deformed according to a patient's body part anatomical contours and cooled to ambient temperature such as to rigidify.

The terms "support fixation surface" and "fixation surface" are used herein as synonyms and refer to a surface to which the device according to the present invention is suitable to be mounted and/or fixed. Said fixation surface might be a radiation table for instance.

In a first aspect, the present invention provides a method for non-invasive stereotactic immobilization of a patient body part for radiotherapy applications comprising the steps of:
  mounting a device comprising a flanged support member to a fixation surface; said flanged support member is adapted to receive and retain at least two sheets;
  mounting a first sheet to the flanged support member;
  placing the patient body part to be immobilized on said first sheet thereby covering the anatomical contours of a first area of said body part; and
  mounting a second sheet to the flanged support member thereby covering the anatomical contours of a second area of said body part which is not covered by the first sheet.

The method is adapted for supporting the immobilized body part free from the fixation surface by the two sheets and the device. This means that the immobilized body part is not in contact with the fixation surface but is separated from said surface by a distance d.

In a preferred embodiment, the first and the second sheets are suitable to be formed on the patient body part such as to conform the anatomical contours of said patient body part.

In another preferred embodiment, the first and the second sheets are pre-formed sheets which are conform to the anatomical contours of the patient body part. The method according to an embodiment of the invention can further comprise the step of scanning the body part for pre-forming the first and the second sheets. This embodiment will be further detailed later.

Wherein the first and the second sheets are suitable to be formed on the patient body part, moldable thermoplastic sheets might be used. In this embodiment, the method comprises the following subsequent steps:
  mounting a device 1, FIG. 1 to a support fixation surface 7, FIG. 3 such as a table for radiation therapy. As shown in FIG. 1, the device 1 comprises a bottom plate 2 having fixation means 6 for mounting said bottom plate 2 to the support fixation surface; a flanged support member 3 having a plurality of attachment means 5 adapted to receive at least two moldable thermoplastic sheets; said bottom plate 2 is connected to said flanged support member 3 by an open structure which preferably comprises a plurality of upstanding circumferential support legs 4,
  Heating and mounting a first moldable thermoplastic sheet to the flanged support member 3 of the device 1,
  Placing the patient body part to be immobilized on said first heated moldable thermoplastic sheet such as to deform the first moldable thermoplastic sheet into a shape which is conform to the anatomical contours of a first area of the patient body part and in an optimized position for the radiation dose delivery with respect to the critical organs and which covers said first area. If the head of the patient is to be immobilized, the patient lays the back of his head (parietal and occipital bone) into the first heated thermoplastic sheet. The first thermoplastic sheet will conform to the anatomical contours of the back of the patient's head and the desired position and rotation in the XZ and YZ plane,
  Cooling the first moldable thermoplastic sheet to ambient temperature to rigidify the deformed first moldable thermoplastic sheet. The cured thermoplastic sheet will have the same shape as the back or the front head of the patient,
  Heating and mounting a second moldable thermoplastic sheet to the flanged support member 3 of the device 1 such as to deform said second moldable thermoplastic sheet into a shape which is conform and covers the anatomical contours of a second area of the patient body part which is not covered by the first area. If the first thermoplastic sheet was used to conform to the anatomical contours of the back of the head, than the second thermoplastic sheet will be used to conform to the front of the head (the patient's face),
  Cooling the second moldable thermoplastic sheet to ambient temperature to rigidify the deformed second moldable thermoplastic sheet. The patient remains in the same position during the production of the double shell mask. This means that, for mounting the second thermoplastic sheet, the patient is maintained in the same position as for mounting the first thermoplastic sheet.

In a preferred embodiment, when the patient body part to be immobilized is placed on the first heated moldable thermoplastic sheet, a pressure is applied on said body part. The pressure is applied such as to conform the first elastic sheet to the anatomical contours of a first area of the patient body part. Said pressure should be applied with care as it should high enough to conform the sheet to the body part and simultaneously, it should not be too high to avoid bringing the patient body part in contact with the fixation surface. This is due to the low elasticity of the first thermoplastic sheet which will be further detailed.

In a preferred embodiment, the second heated moldable thermoplastic sheet is only brought in contact with the patient's body part without pressing it against said body part. The second sheet is provided with high elasticity such as it conforms the patient's body part anatomical contours without pressure requirement. In some cases and wherein the face is covered by the second sheet, it might be required to apply a pressure on the bone of the nose to conform the sheet to the nose of the patient.

The cured first and second thermoplastic sheets form an immobilization double shell mask covering the entire head of the patient. The double shell mask is personalized to the patient's head anatomy. In a preferred embodiment of the method, for mounting the second thermoplastic sheet, the patient is maintained in the same position as for mounting the first thermoplastic sheet. This is advantageous as a high level of stability is ensured during the production of the immobilization double shell mask, thereby providing a better fit of the mask to the anatomical contours of the patient's head.

In a preferred embodiment, when mounted on the device 1, the first moldable thermoplastic sheet 11 is not supported in its central region but is only circumferentially supported by the flanged support member. This is achievable as the first thermoplastic sheet 11 has a rigidity that allows providing a sufficient force to support the rear or the front head and simultaneously providing a sufficient elasticity such as to deform the sheet according to the anatomical contours of the rear or the front head. After cooling, the cured first thermoplastic sheet will be separated from the bottom plate 2 by an open accessible space. Said open accessible space is created underneath the cured first thermoplastic sheet. The device of the present invention is designed such as the cured first thermoplastic sheet will not be in contact with the bottom plate 2. This is advantageous as the thermoplastic sheet will deform according to only and solely the patient's head shape. In addition, the practitioner will have access and will be able to touch, support and shape the thermoplastic sheet when the patient's head is placed on the other surface of the sheet. The practitioner can than make sure that the sheet is perfectly matching the anatomical contours of the head.

In a preferred embodiment, when mounted on the device 1, the first moldable thermoplastic sheet 11 is not supported in its central region by a cushion for instance but is only circumferentially supported by the flanged support member. The first thermoplastic sheet 11 can have a single contact point with the bottom plate. This is achievable as the first thermoplastic sheet 11 has a rigidity that allows providing a sufficient force to support the rear or the front head and simultaneously providing a sufficient elasticity such as to deform the sheet according to the anatomical contours of the rear or the front head. This is advantageous as the thermoplastic sheet will deform according to only and solely the patient's head shape.

In a preferred embodiment, taking as reference the bottom plate of the device, the closest point of the first cured thermoplastic sheet is separated from the bottom plate by a free empty distance d (not shown). Said distance is measured perpendicular to the plane of the bottom plate. In a preferred embodiment, the distance d is comprised between 0.2 and 25 cm, preferably between 0.5 and 12 cm, more preferably between 1 and 18 cm, even more preferably between 2 and 6 cm, most preferably between 1 and 4 cm.

In a preferred embodiment, the first and/or the second thermoplastic sheet might be provided with one or more openings. For instance an opening can be provided in the sheet covering the face of the patient. Said opening will be positioned such as to be at the level of the nose and/or the mouth such as to permit the patient to breathe.

In a preferred embodiment, the first and the second moldable thermoplastic sheets are heated at a temperature comprised between 70 and 90° C., preferably between 65 and 85° C. The sheets may be softened by warming them to a temperature above their glass transition temperature, for instance by immersion in warm water, at which temperature they becomes shapeable. In a preferred embodiment, the sheets are warmed by immersion in an aqueous liquid having a temperature comprised between 70-90° C. As described above, the sheets are allowed to cool below their glass transition temperature, preferably to ambient temperature of 20° C. to 30° C. The sheets will rigidify and provide a form-fitting double shell mask.

Although warming of the thermoplastic sheets 11, 11' above their glass transition temperature will cause the sheets to become stretchable and deformable, they can be transported without damage by taking hold of the circumferential rims 12, 12' of the sheets and displacing them on the flanged support member 3 of the device 1. Said circumferential rims 12, 12' can be permanently fixed to the moldable thermoplastic sheets or can be dismountably fixed to said sheets. The latter configuration is advantageous as it allows optimizing the cleaning of the sheets both in their initial and final state. Furthermore, dismountable circumferential rims can be easily changed by new rims if required, for instance if the rim is damaged.

In a second aspect, the present invention provides a device for immobilization of a patient body part for radiotherapy applications. The device comprises at least one flanged support member 3 suitable to receive and retain two sheets. The sheets can be moldable thermoplastic sheets or pre-formed sheets or any other sheets suitable to be used in the context of the present invention and known to the person skilled in the art.

Preferably, the flanged support member is suitable to be mounted on a fixation surface using support member fixation means, such as said flanged support member is mounted and at a distance d from said fixation surface. In a preferred embodiment, the flanged support member is mounted substantially parallel to the fixation surface. Preferably, the flanged support member is mounted such as to be contained in a plane which is substantially parallel to the plane of the fixation surface.

In a preferred embodiment, the flanged support member fixation means are selected from the group comprising upstanding circumferential support legs, upstanding walls provided with openings, upstanding pyramids, inverted pyramids or any other flanged support member fixation means known to the person skilled in the art. Said flanged support member fixation means can be of any shape. The height of said flanged support member fixation means should be selected such as a free space between the fixation surface and the sheet when the body part is immobilized. For example, referring to FIG. 16, the height of the flanged support member fixation means, i.e. upstanding circumferential support legs 4, is higher than the distance separating the rim 12 of the sheet 11 from the point which is most distal to said rim 12. The distance is measured perpendicularly to the rim 12. It is to be understood that said distance is measured differently according to the immobilized body part and/or according to the position in which said body part is immobilized.

In a preferred embodiment, the device comprises a bottom plate. Preferably said bottom plate is permanently or dismountably connected to said flanged support member by the flanged support member fixation means. The bottom plate is provided with fixation means for mounting said bottom plate to a fixation surface.

In a preferred embodiment, the device comprises at least one flanged support member 3 having a plurality of attachment means 5 adapted to receive at least two sheets or two moldable thermoplastic sheets. The plane of the bottom plate and the plane of the flanged support member are substantially parallel to each other or form 2 angled planes to preposition the patient's body part depending on the treatment. The device might comprise a bottom plate 2 which is connected to said flanged support member 3 by an open structure which preferably comprises a plurality of upstanding circumferential support legs 4 (FIG. 1).

In a preferred embodiment, the open structure preferably comprising a plurality of upstanding circumferential support legs 4 or the flanged support member fixation means separates the plane of the bottom plate or the plane of the fixation surface from the plane of the flanged support member by a distance d comprised between 5 and 100 cm, preferably between 10 and 90 cm, more preferably between 15 and 80 cm, even more preferably between 20 and 70 cm, most preferably between 25 and 60 cm, even most preferably between 30 and 50 cm.

In a preferred embodiment, the upstanding circumferential support legs 4 are separated from each other by a distance comprised between 8 and 30 cm, preferably between 10 and 20 cm. In a preferred embodiment, the device is provided with 2 to 20, preferably 3 to 15, more preferably 4 to 10 upstanding circumferential support legs. In a preferred embodiment, the device comprises at least 6 upstanding circumferential support legs. The support legs consist of a Uni Directional carbon fiber tube with a wall thickness of 0.2-2.0 mm and a weight between 150 and 250 gr/m$^2$. For optimal dosimetric properties, the wall thickness is between 0.2 and 0.5 mm. The support legs might be glued to the flanged support member and/or to the bottom plate. In the gluing areas the tubes are filled with low density foam, e.g. Rohacell 51 or 71, with a maximum length of 10-15 mm.

In a preferred embodiment, the upstanding circumferential support legs are substantially perpendicular to the bottom plate 2 and/or to the flanged support member and are separated from each other, at the level of the bottom plate 2, by a distance D comprised between 8 and 30 cm, preferably between 10 and 20 cm.

In a more preferred embodiment, the upstanding circumferential support legs form an angle α (shown in FIG. 1 and FIG. 16) with the bottom plate 2 such as α is at least 90° and is comprised between 90° and 150°, preferably between 100° and 140° More preferably between 110° and 135°. In this embodiment, the upstanding circumferential support legs are also separated from each other, at the level of the bottom plate 2, by a distance D comprised between 8 and 30 cm, preferably between 10 and 20 cm.

Figure 2:
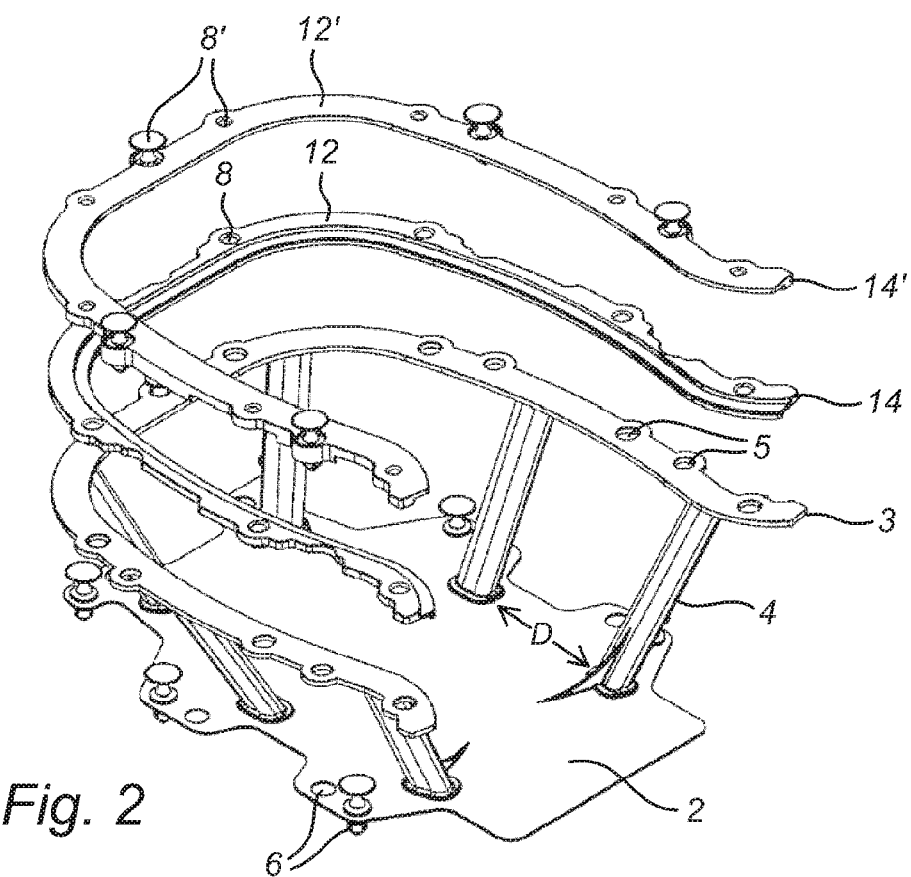
FIG. 2 shows the device and the circumferential rims of the thermoplastic sheets according to the present invention.

In a preferred embodiment, the flanged support member 3 of the device has preferably a flat shape (FIG. 1). The flanged support member 3 is adapted to receive at least two sheets or two moldable thermoplastic sheets having each a circumferential rim (will be detailed further). In a preferred embodiment, the circumferential rims of both sheets or thermoplastic sheets and the flanged support member are, at least partially, superimposable (as shown in FIG. 2).

In a preferred embodiment, the device of the present invention has a shape which is open at one end; said shape is preferably a U shape. In a preferred embodiment, the flanged support member 3 and the circumferential rims 12, 12' presented in the figures have a U shape as said figures show a device adapted for immobilizing a human head. It is to be understood that the flanged support member 3 and the circumferential rims 12, 12' can have any other shape adapted to immobilize any other part of a human body. For instance the device might comprise two flanged support members having a shape which is parallel to the contours of the trunk of a patient. The two flanged support members might be linear members whereby one member is placed at the right and the other member is placed at the left of the body part to be immobilized.

In a preferred embodiment, the flanged support member is provided with attachment means 5. Preferably, the attachment means 5 of the flanged support member are selected from the group comprising: snap fit means connections and openings for receiving rivets, screws or bolts (FIG. 1). In a preferred embodiment, the flanged support member is provided with 5 to 30, preferably 10 to 25, more preferably 12 to 22 attachment means.

Figure 3:
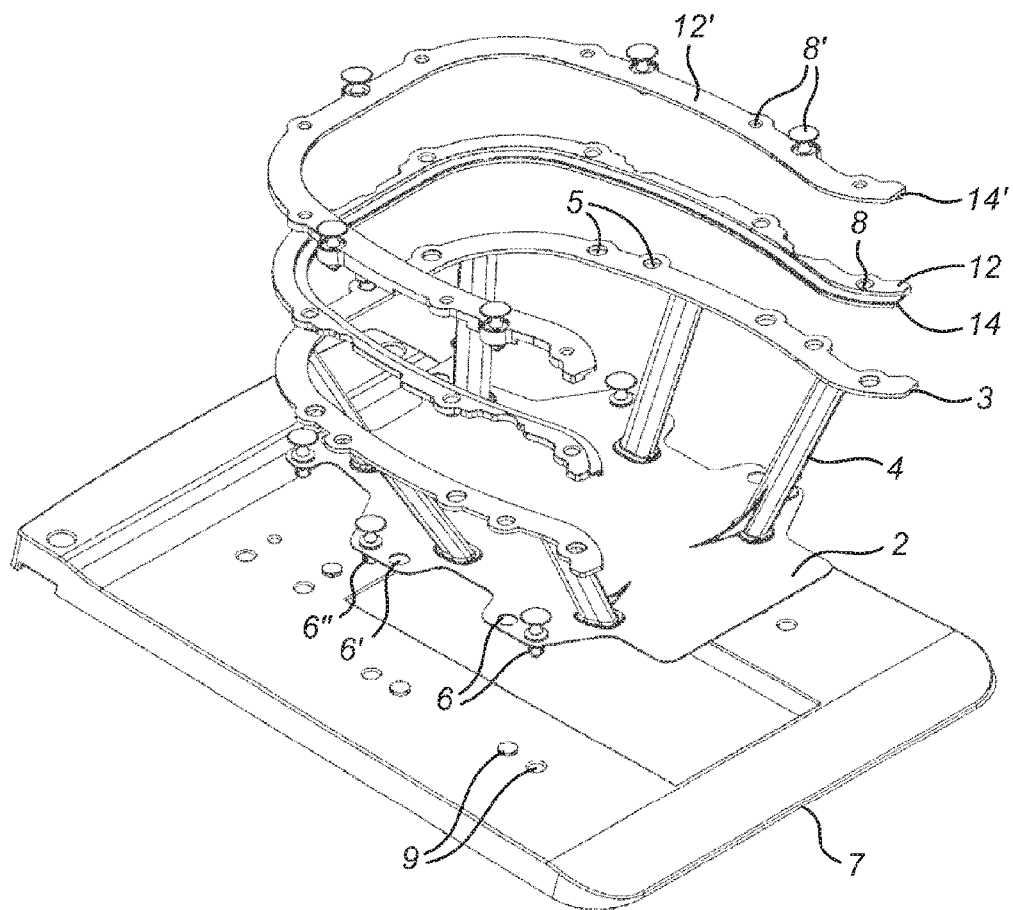
FIG. 3 shows the support fixation surface, the device and the circumferential rims of the thermoplastic sheets according to the present invention.

In a preferred embodiment, the bottom plate 2 is provided with fixation means 6 for mounting the bottom plate 2, and hence mounting the device, to a support fixation surface 7 such as table for radiation therapy (FIG. 3). The support fixation surface 7 is also provided with support surface fixation means 9 which correspond to the bottom plate fixation means 6 (FIG. 3). The fixation means of the bottom plate and the corresponding fixation means of the support fixation surface are selected from the group comprising: rivets, screws, bolts and nuts, and snap fit means connections and foam or plastic pads or parts that will fit in recesses in the support fixation surface or baseplate. Preferably, the fixation means 6 of the bottom plate 2 comprise snap fit connections and rivets. More preferably said provided snap fit connections 6' and rivets 6" are provided in an intermittent pattern (FIG. 3). In a preferred embodiment, the bottom plate is provided with 3 to 30, preferably 5 to 25, more preferably 10 to 20 fixation means. Wherein the flanged support member is mounted on the fixation surface using flanged support member fixation means, the fixation surface is adapted to receive and fix said fixation means.

The bottom plate of the device according to an embodiment of the invention can have different shapes. Each shape will be adapted to fit to a specific position of the head including the positions wherein the chin is in the air, the position wherein the chin is on the chest and the prone position. This variation accomplishes and secures the most desired position of the head to avoid critical organs in the radiation field. The shape might also be adapted and fitted for any other part of the body. The bottom plate of the device according to an embodiment of the present invention can also have different shapes. Each shape will be adapted to fit to different support fixation surfaces or baseplates.

In a preferred embodiment, the device is manufactured from a material having a low density. In a further preferred embodiment, the device is manufactured from a carbon composite material, more preferably from a carbon composite polymer, most preferably from carbon fiber reinforced plastics. This is advantageous as the device will have a low specific weight while having the necessary strength for holding the patient's head during the production of the double shell mask. In a preferred embodiment, the weight of the device is comprised between 50 and 1000 g, preferably between 100 and 900 g, more preferably between 150 and 800 g.

In a third aspect, the present invention provides a system for immobilization of a patient body part for radiotherapy applications comprising a device comprising at least one flanged support member which is suitable to be mounted to a fixation surface and is adapted to receive and retain at least two sheets; a first sheet for covering the anatomical contours of a first area of said body part, and a second sheet for covering the anatomical contours of a second area of said body part which is not covered by the first sheet. The system is adapted for supporting the immobilized body part free from the fixation surface by the two sheets and the device.

Free from the fixation surface refers to the fact that the immobilized body part is not in contact with the fixation surface but is separated from said surface by a free space.

Figure 4:
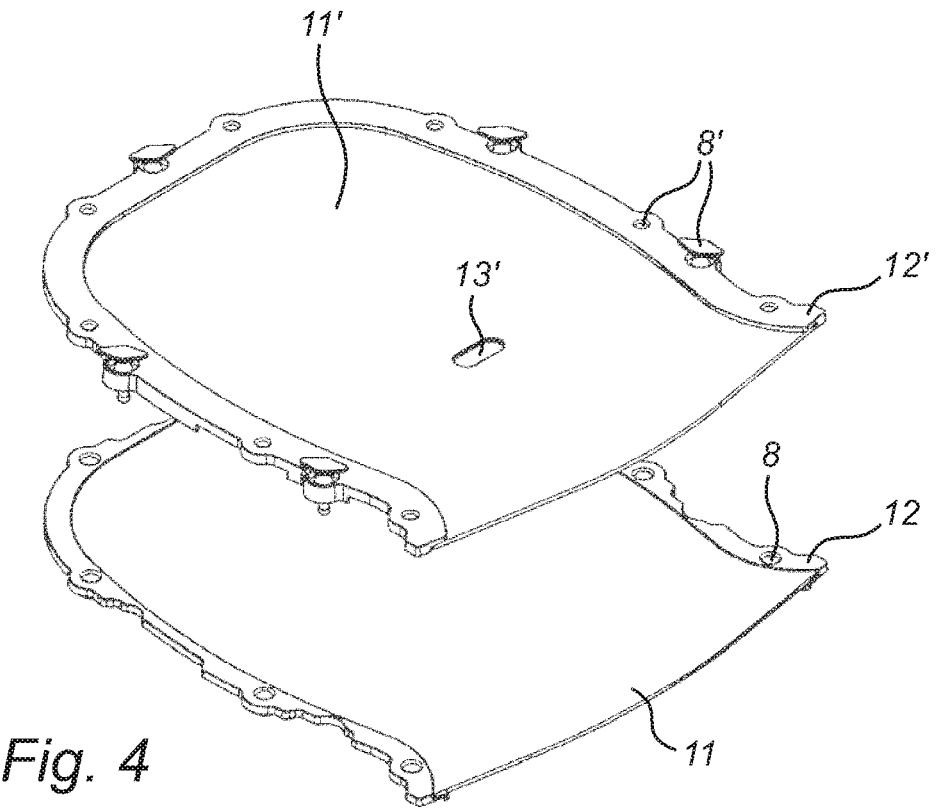
FIG. 4 shows two different moldable thermoplastic sheets designed to be super imposable according to the present invention.
Figure 7:
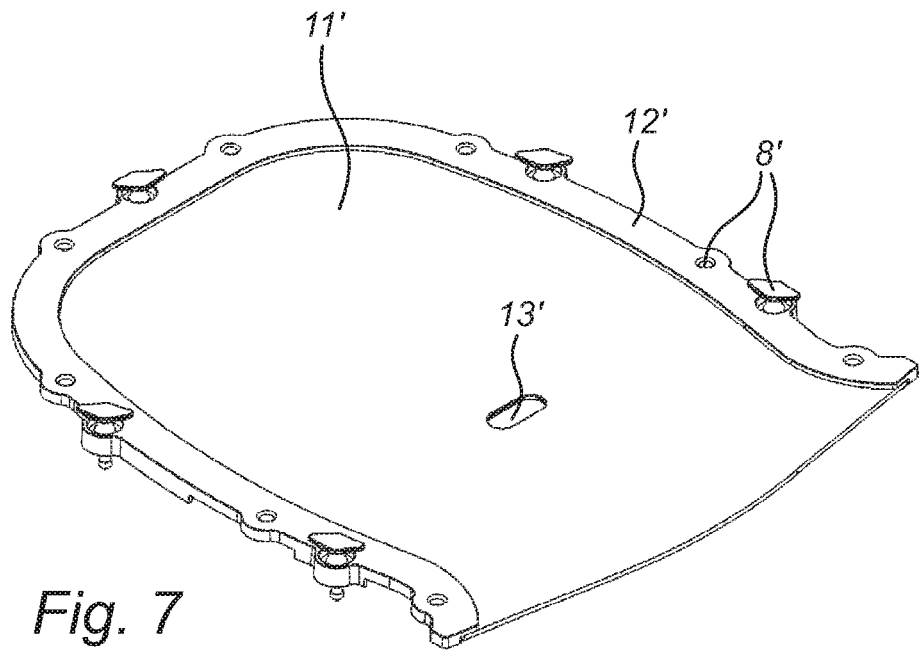
FIG. 7 shows another moldable thermoplastic sheet in initial state according to the present invention.

In a preferred embodiment, the system for immobilization of a patient body part comprises: a device 1 comprising a bottom plate 2 and a flanged support member 3 adapted to receive at least two moldable thermoplastic sheets, said bottom plate 2 and flanged support member are connected by a an open structure, preferably comprising a plurality of upstanding circumferential support legs 4 (FIG. 1); a first moldable thermoplastic sheet (11, FIGS. 4 and 5); and a second moldable thermoplastic sheet (11', FIGS. 4 and 7). In a preferred embodiment, the first and the second moldable thermoplastic sheets 11, 11' are designed to be superimposable (FIG. 4).

In a preferred embodiment, the first sheet is designed and/or molded to conform the anatomical contours of the first area of the body part and the second sheet is designed and/or molded to conform the anatomical contours of the second area of the body part thereby forming a double shell mask enclosing said body part.

In a preferred embodiment, the flanged support member is provided with a plurality of attachment means adapted to receive and retain the sheets. In a preferred embodiment, the system comprises at least one flanged support member fixation means for mounting the flanged support member of the device to the fixation surface at a distance from said fixation surface, thereby mounting the flanged support member substantially parallel to the fixation surface.

Figure 4A:
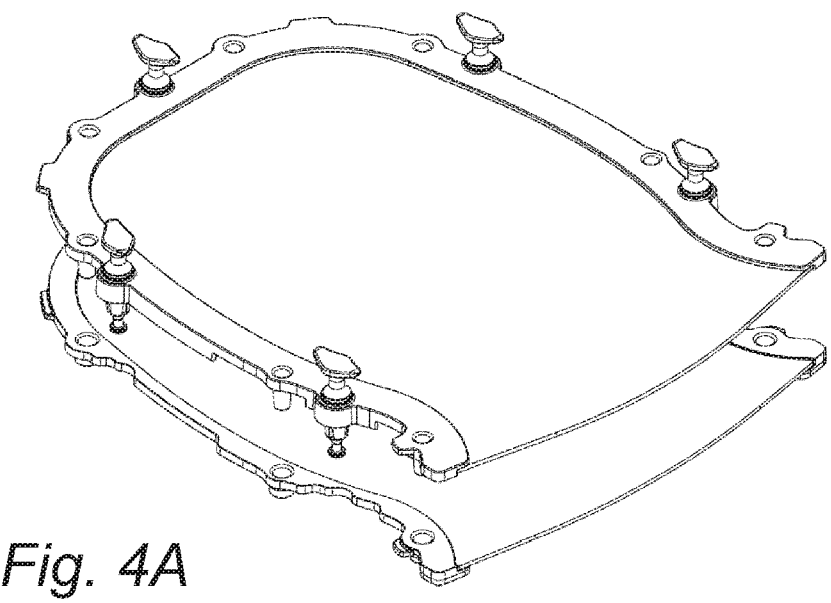
FIG. 4A shows another embodiment of two different moldable thermoplastic sheets designed to be super imposable according to the present invention.

In a preferred embodiment, the first sheet and the second sheet comprise each a circumferential rim having a number of connection means for mounting said sheets to the flanged support member. In a preferred embodiment, the first and the second sheets or moldable thermoplastic sheets (11, 11') comprise each a circumferential rim 12, 12' having a number of connection means 8, 8'. In a further preferred embodiment, the circumferential rims 12, 12' of the first and the second sheets or moldable thermoplastic sheets 11, 11' are designed to be superimposable (FIG. 4). In a preferred embodiment, at least one of said sheets or thermoplastic sheets 11' is provided with at least one opening 13' for the patient's month as shown in FIG. 4. In another embodiment, both sheets are devoid of openings as shown in FIG. 4A.

The connection means 8, 8' of the circumferential rims 12, 12' of the sheets or the thermoplastic sheets are selected from the group comprising: rivets, screws, bolts and nuts, and snap fit means connections or any other type of connections means known to the person skilled in the art. The connection means 8, 8' can also be simply openings wherein a fastening means such as rivets or bolts can be introduced and used. In a preferred embodiment, each circumferential rim is provided with 3 to 30, preferably 5 to 25, more preferably 10 to 20 connection means.

In a preferred embodiment, the connection means 8 of the circumferential rim 12 of the first sheet or first thermoplastic sheet 11 are positioned such as to correspond to all or to a part the connection means 8' of the circumferential rim 12' of the second sheet or second thermoplastic sheet and/or to all or to a part of the attachment means 5 of the flanged support member 3 of the device 1 when the first and the second sheets or thermoplastic sheets are simultaneously attached to the flanged support member 3.

In a preferred embodiment, the connection means 8' of the circumferential rim 12' of the second sheet or second thermoplastic sheet 11' are positioned such as to correspond to all or to a part of the connection means 8 of the circumferential rim 12 of the first sheet or first thermoplastic sheet and/or to all or to a part of the attachment means 5 of the flanged support member 3 of the device 1 when the first and the second thermoplastic sheets are simultaneously attached to the flanged support member 3.

In a preferred embodiment, the connection means 8, 8' are positioned on the circumferential rims 12, 12' such as to correspond intermittently with all or with a part of the attachment means 5 of the flanged support member 3. For instance, each attachment means 5 of the flanged support member 3 corresponding with a connection means 8 of the first sheet or thermoplastic sheet 11 will have a left and right neighboring attachment means that correspond with two connection means 8' of the second sheet or second thermoplastic sheet 11'. Similarly, each attachment means 5 of the flanged support member 3 corresponding with a connection means 8' of the second sheet or second thermoplastic sheet 11' will have a left and right neighboring attachment means that correspond with two connection means 8 of the first sheet or first thermoplastic sheet 11.

In a preferred embodiment, the first sheet or first moldable thermoplastic sheet has a shear modulus—or rigidity—which is higher than the shear modulus of the second sheet or second moldable thermoplastic sheet. In a preferred embodiment, the ratio=shear modulus of the first moldable thermoplastic sheet/shear modulus of the second moldable thermoplastic sheet is at least 1.05, preferably at least 1.1, more preferably at least 1.2, even more preferably at least 1.3, most preferably at least 1.4, even most preferably at least 1.5. Said ratio is at most 5, preferably at most 4, more preferably at most 3, even more preferably at most 2.5, most preferably at most 2, even most preferably at most 1.8.

Figure 5:
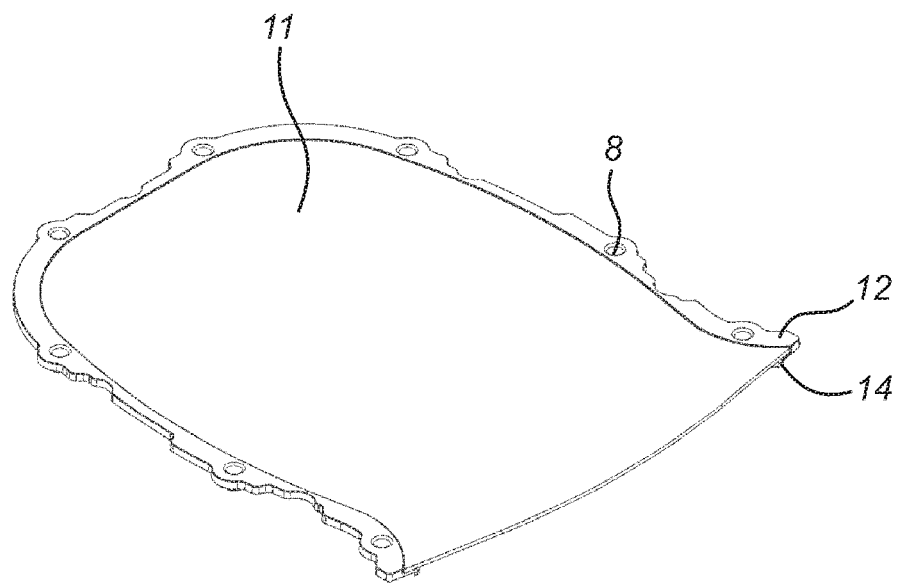
FIG. 5 shows a moldable thermoplastic sheet in initial state according to the present invention.
Figure 6:
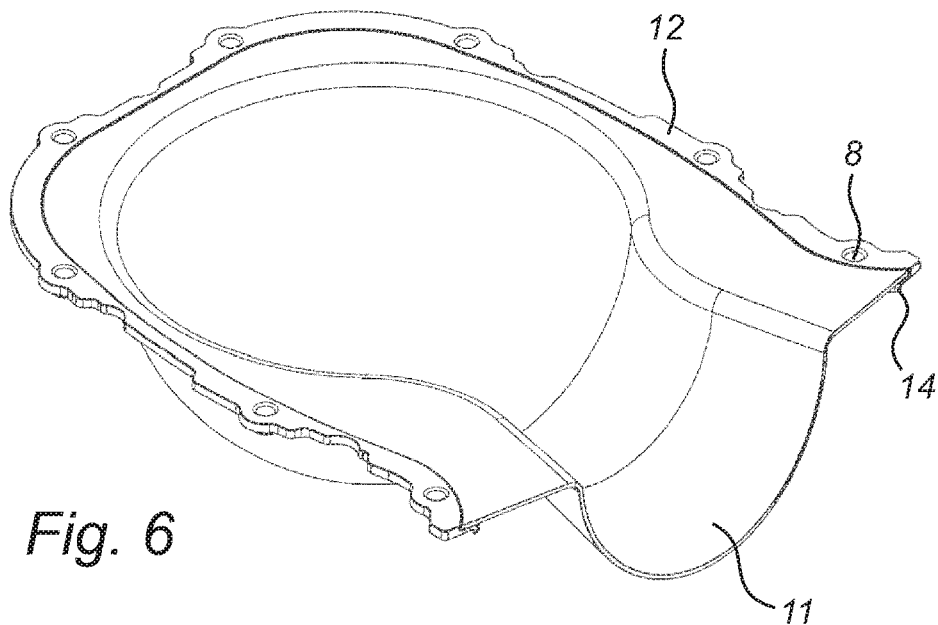
FIG. 6 shows the thermoplastic sheet of FIG. 5 in final state, after molding on a patient's body part and curing.

In use, the device 1 is fixed to the support fixation surface 7 using the fixation means 6 and the support surface fixation means 9. Then, the first thermoplastic sheet 11, FIG. 5 is heated and fixed, via the connection means 8 of its circumferential rim 12, to the flanged support member 3 attachment means 5. In addition, the recess 14 of the first thermoplastic sheet 11 can be used for fixing said sheet on an edge of the flanged support member 3. The patient is then placed with his rear head or his front head, on the heated first moldable thermoplastic sheet such as to deform the sheet according to the anatomical contours of the rear or the front head. The first thermoplastic sheet 11 is then allowed to cool down such as to obtain a cured first thermoplastic sheet 11 as shown in FIG. 6.

Figure 8:
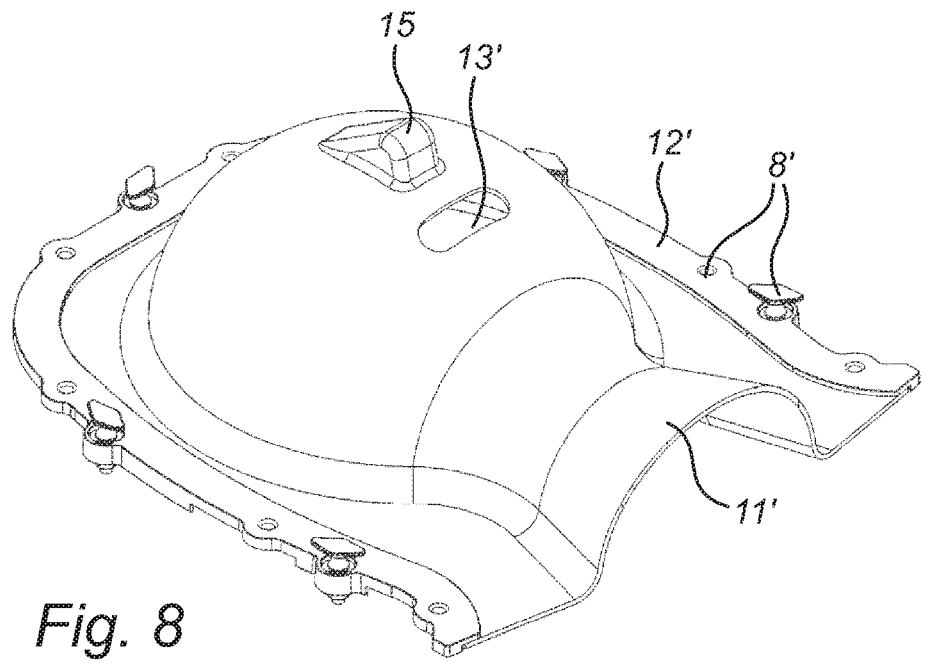
FIG. 8 shows the thermoplastic sheet of FIG. 7 in final state, after molding and curing.
Figure 8A:
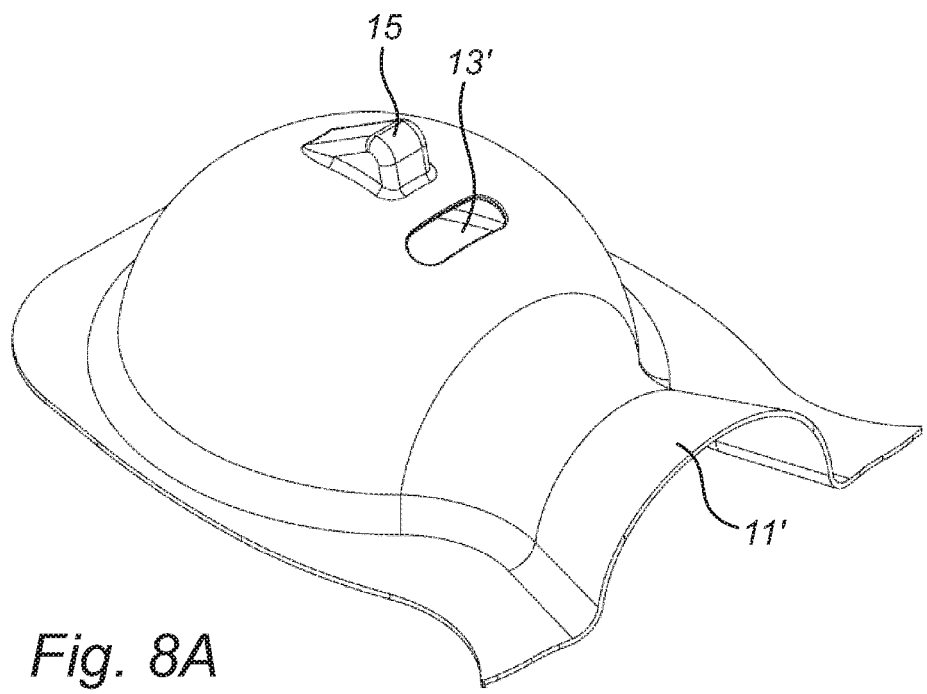
FIG. 8A shows the thermoplastic sheet of in final state, after molding and curing. The sheet is devoid of circumferential rim.

Afterwards, the second thermoplastic sheet 11', FIG. 7 is heated and fixed, via the connection means 8' of its circumferential rim 12', to the flanged support member 3 attachment means 5. In addition, the recess 14' of the first thermoplastic sheet 11' can be used for fixing said sheet on an edge of the flanged support member 3. The second thermoplastic sheet will then cover the part of the head (rear or front head) which was not covered by the first thermoplastic sheet 11. The heated second thermoplastic sheet 11' will deform according to the anatomical contours of the rear or the front head. The second thermoplastic sheet 11' is then allowed to cool down such as to obtain a cured second thermoplastic sheet 11' as shown in FIG. 8. The cured second thermoplastic sheet 11' shown in FIG. 8 presents a protrusion 15 corresponding to the nose of the patient and is provided with an opening corresponding to the mouth of the patient. It is to be understood that the cured second thermoplastic sheet can be provided with at least two openings wherein the nose protrudes through one opening and the mouth protrudes through the other opening.

Alternatively, when pre-formed sheets are used, the flanged support member is fixed to the fixation surface using the flanged support member fixation means. Then, the first sheet is fixed, via the connection means of its circumferential rim, to the flanged support member attachment means. In addition, the recess of the first sheet can be used for fixing said sheet on an edge of the flanged support member. The patient is then placed with his rear head or his front head, on the first sheet such as to cover a first area of the head. Afterwards, the second sheet is fixed, via the connection means of its circumferential rim, to the flanged support member attachment means. In addition, the recess of the first sheet can be used for fixing said sheet on an edge of the flanged support member. The second sheet will then cover the part of the head which was not covered by the first sheet.

Figure 9:
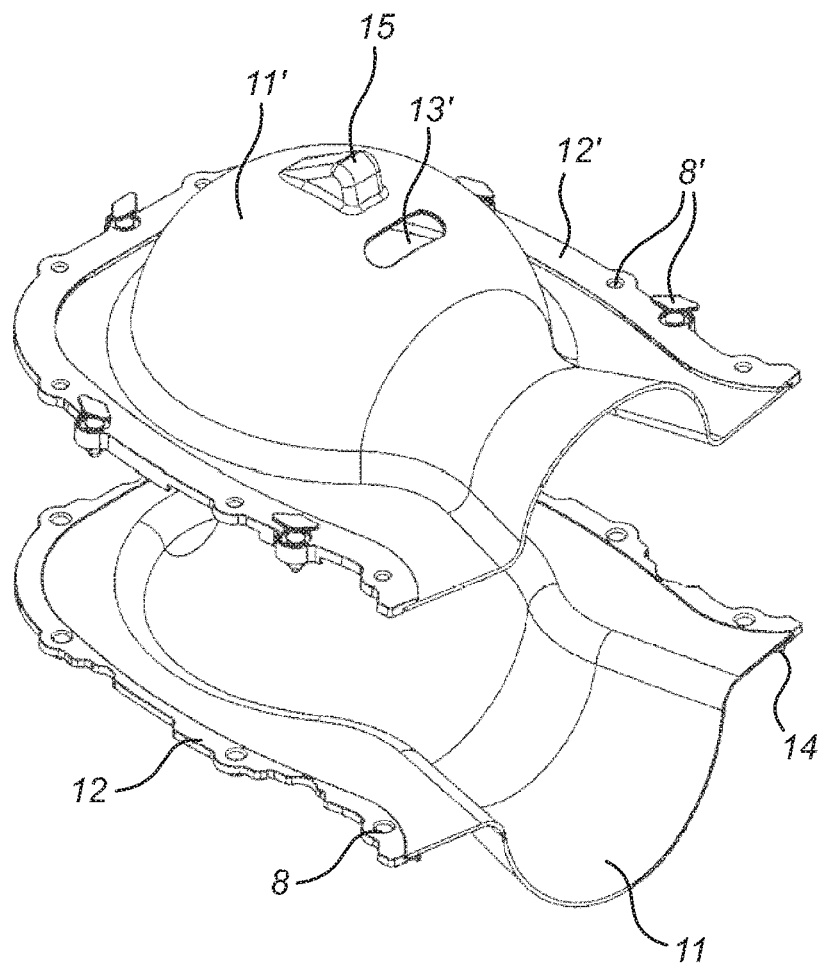
FIG. 9 shows both thermoplastic sheets, as represented in FIG. 6 and FIG. 8, in final state, after molding on a patient's body part and curing.
Figure 10:
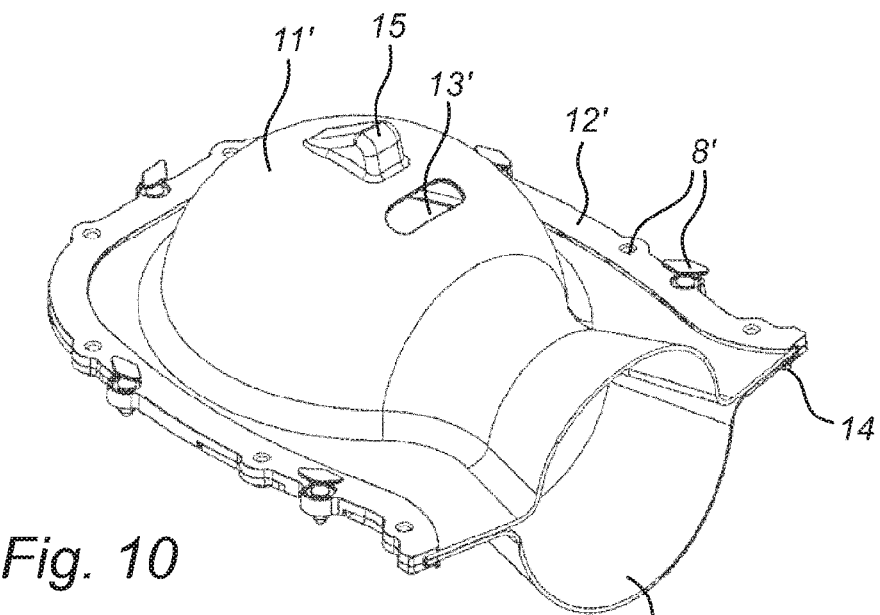
FIG. 10 shows both thermoplastic sheets, as represented in FIG. 6 and FIG. 8, in final state, after molding on a patient's body part and curing. The sheets are superimposed.

FIG. 9 and FIG. 10 respectively show the nonattached and the attached cured first and second thermoplastic sheets 11, 11'. The circumferential rims 12, 12' of said cured sheet are adapted and/or designed to be superimposable.

Figure 11:
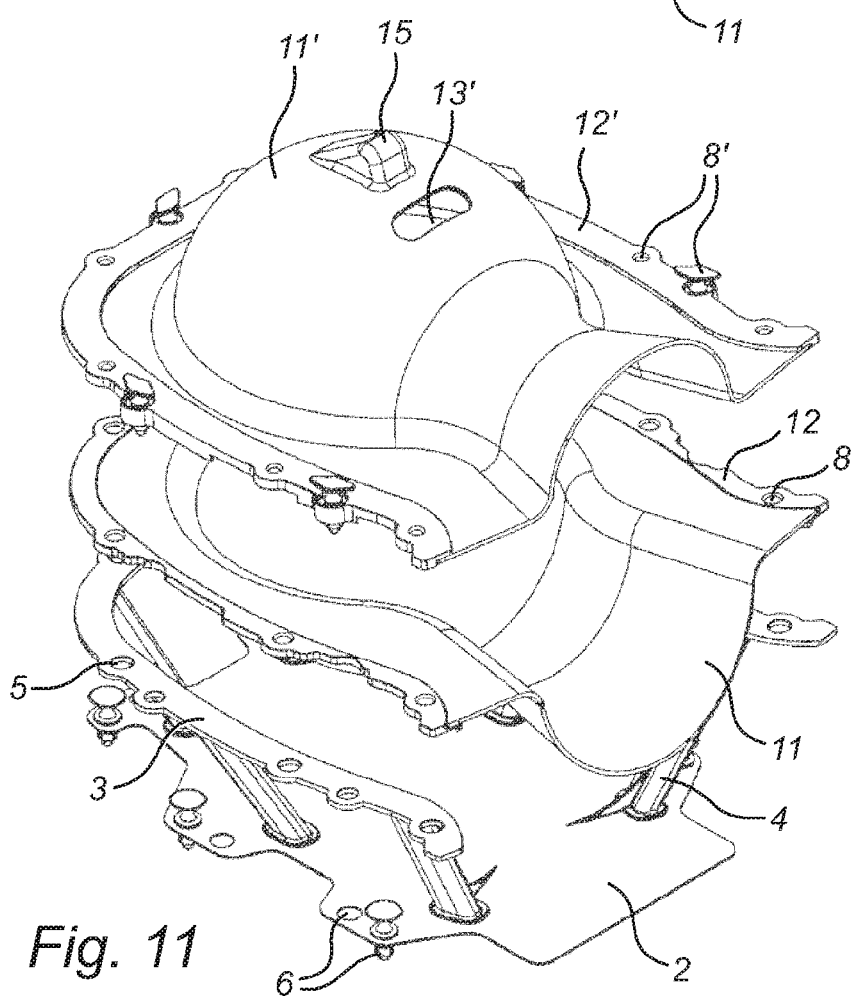
FIG. 11 shows the device and both thermoplastic sheets, as represented in FIG. 6 and FIG. 8, in final state, after molding on a patient's body part and curing.
Figure 12:
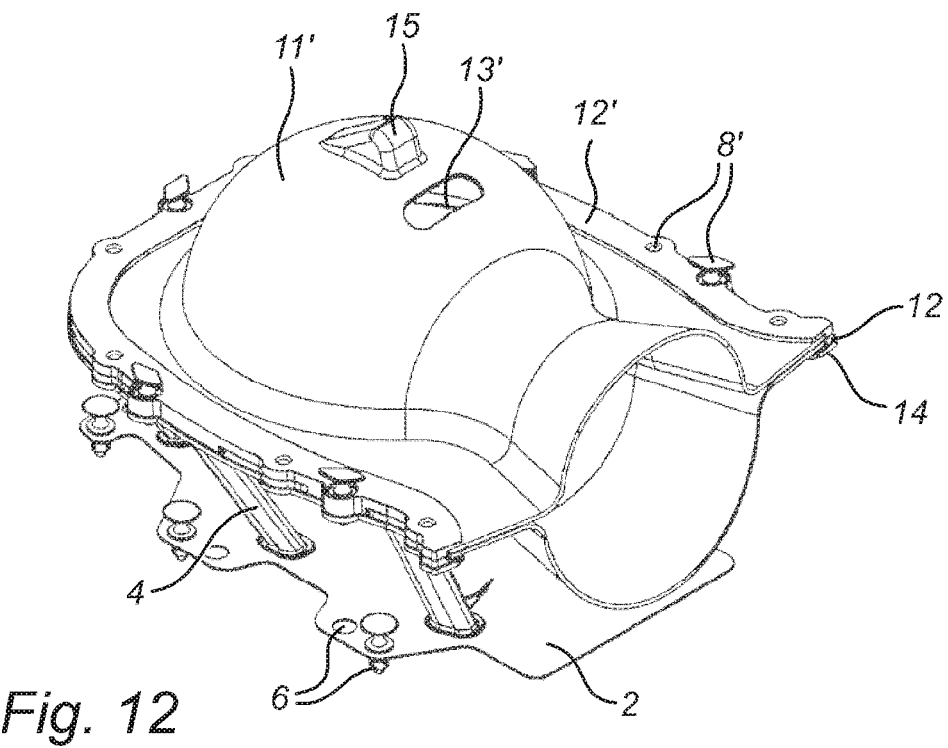
FIG. 12 shows the device and both thermoplastic sheets. The sheets are as represented in FIG. 6 and FIG. 8, in final state, after molding on a patient's body part and curing. The device and the sheets are superimposed.

FIG. 11 and FIG. 12 respectively show the nonattached and the attached cured thermoplastic sheets 11, 11' to the device 1. The superimposable circumferential rims 12, 12' of the cured thermoplastic sheets 11 and 11' are also, at least partially, superimposable and fixable to the flanged support member 3 of the device 1.

Figure 13:
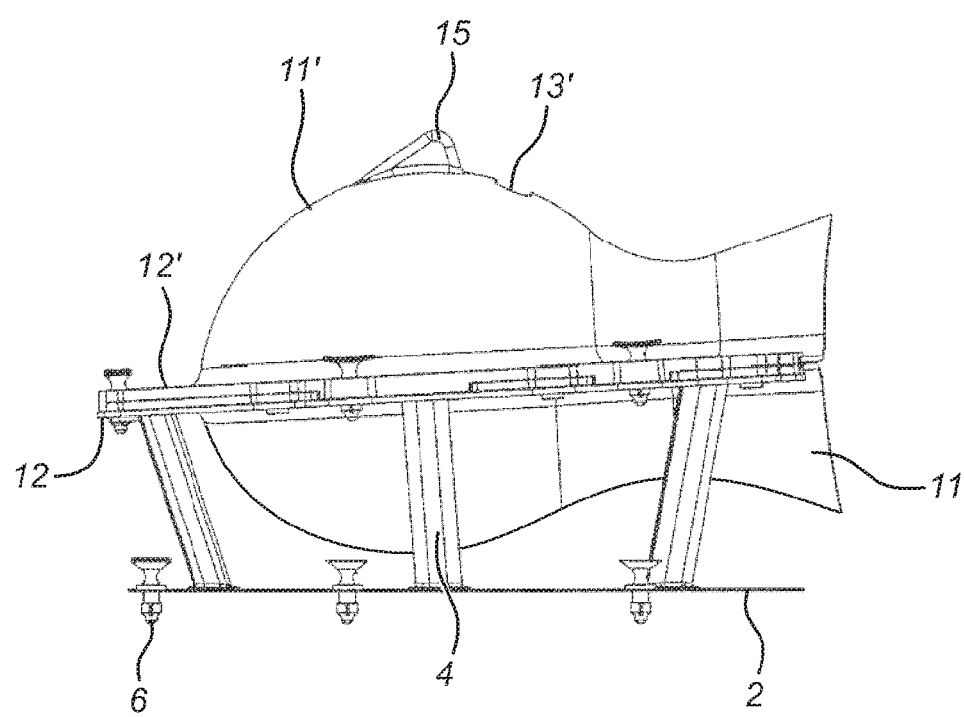
FIG. 13 shows a side view of the superimposed device and both thermoplastic sheets.

FIG. 13 shows a side view of the assembly comprising the device 1 and the cured thermoplastic sheets 11, 11'. The entire head is covered by the double shell mask of the present invention.

Figure 14:
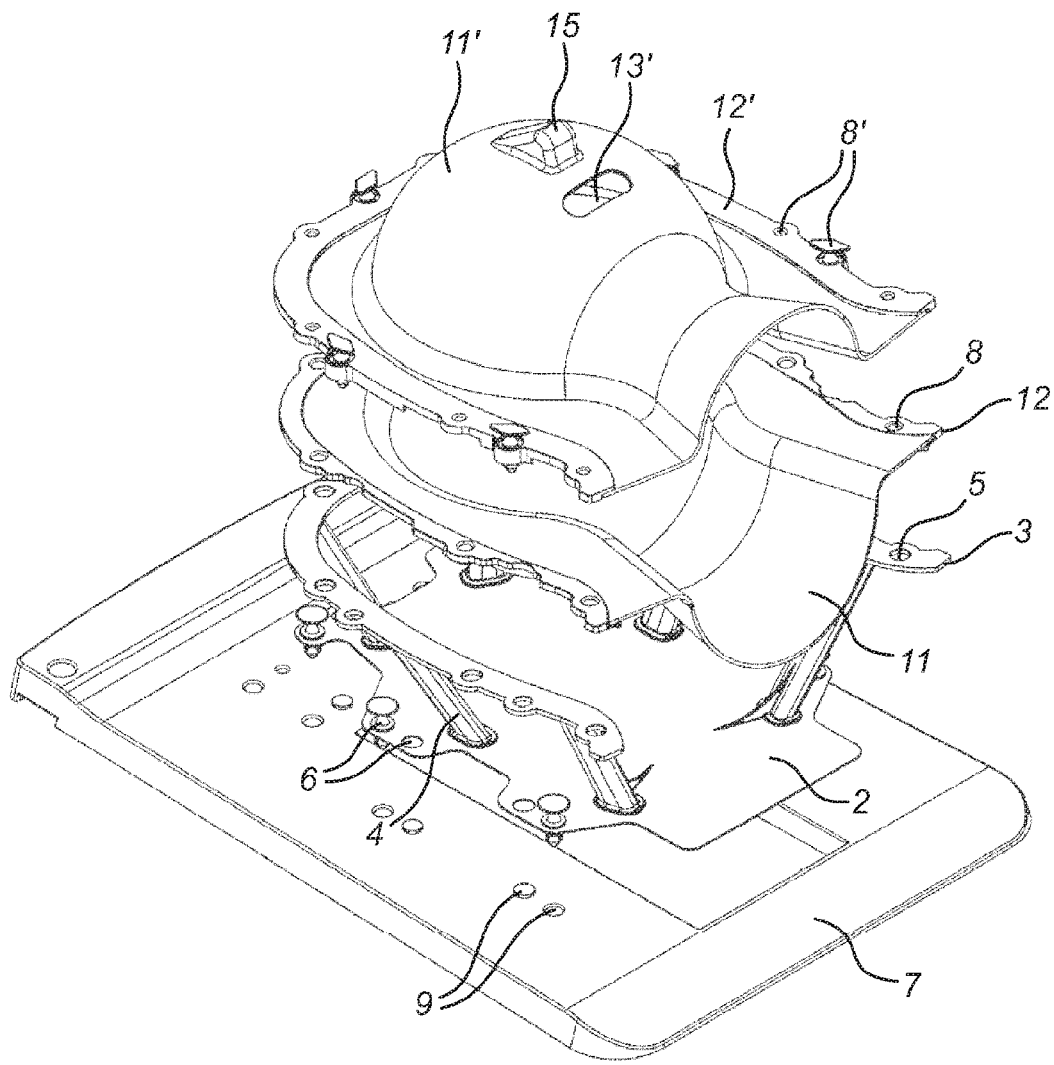
FIG. 14 shows an exploded view of one exemplary embodiment of an assembly comprising a support fixation surface, a device and two thermoplastic sheets constructed according to the present invention. The sheets are as represented in FIG. 6 and FIG. 8, in final state, after molding on a patient's body part and curing.
Figure 15:
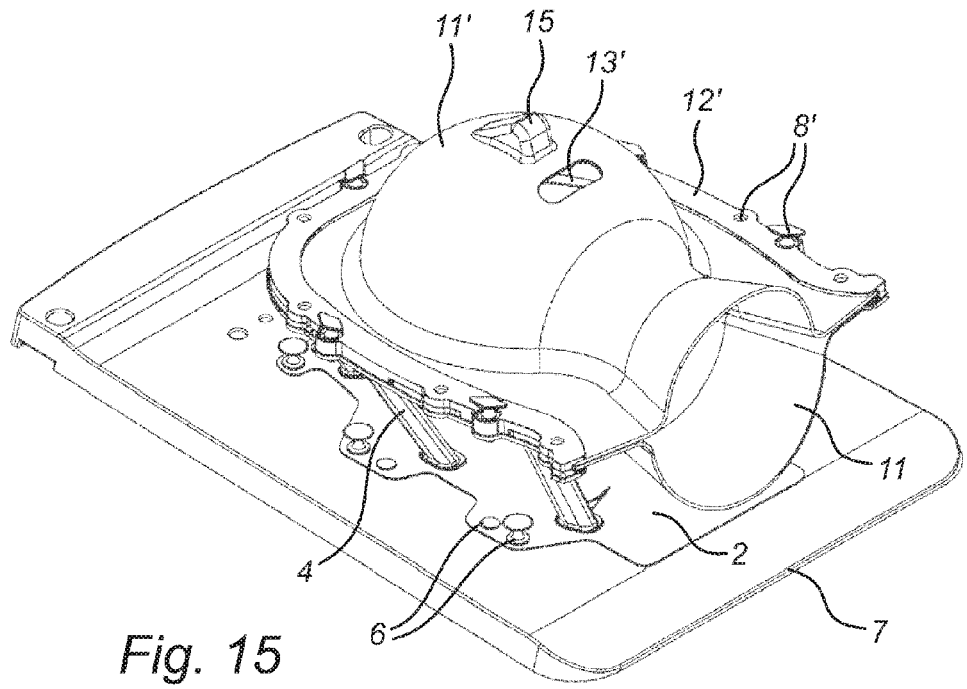
FIG. 15 shows a view of one exemplary embodiment of an assembly comprising a support fixation surface, a device and two thermoplastic sheets constructed according to the present invention. The sheets are as represented in FIG. 6 and FIG. 8, in final state, after molding on a patient's body part and curing. The support fixation surface, the device and both thermoplastic sheets are connected and fixed to each other.

FIG. 14 and FIG. 15 respectively show the nonattached and the attached cured thermoplastic sheets 11, 11' to the device 1 and to the support fixation surface 7. The fixation means 6 of the bottom plate 2 of the device 1 are corresponding to the support surface fixation means 9.

Figure 16:
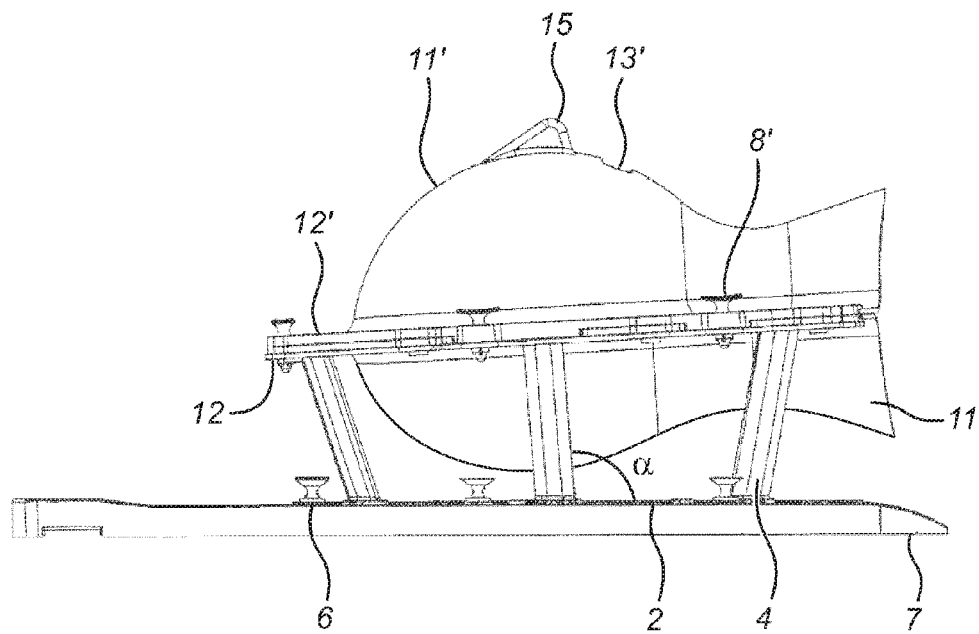
FIG. 16 shows a side view of the exemplary embodiment as shown in FIG. 15. The support fixation surface, the device and both thermoplastic sheets are connected and fixed to each other.

FIG. 16 shows a side view of the assembly comprising the support fixation surface 7, the device 1 and the cured thermoplastic sheets 11,11'. The entire head is covered by the double shell mask of the present invention.

Figure 17:
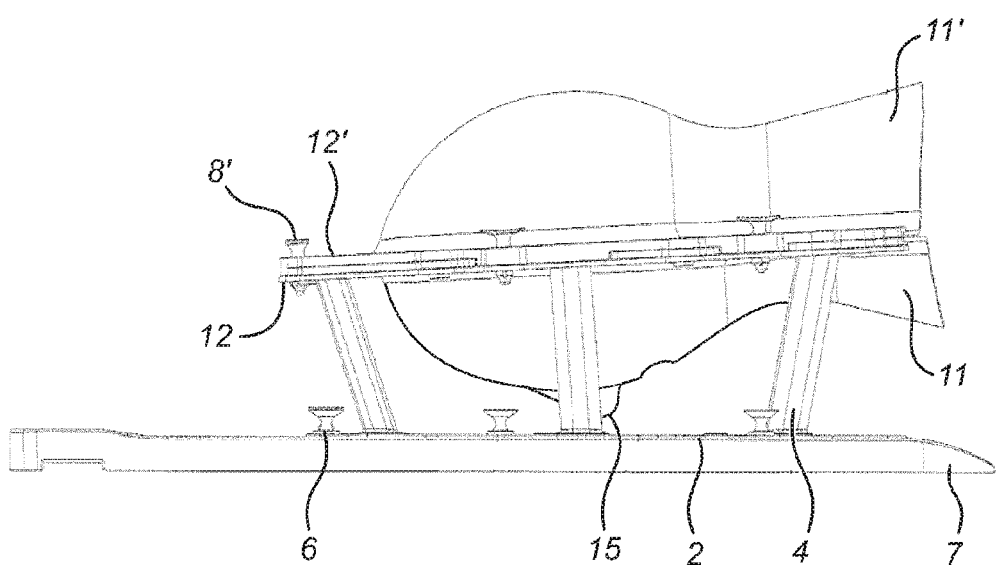
FIG. 17 shows a view of one exemplary embodiment of an assembly comprising a support fixation surface, a device and two thermoplastic sheets constructed according to the present invention. The support fixation surface, the device and both thermoplastic sheets are connected and fixed to each other and are used for the immobilization of a patient's head while the patient is in prone position.

It is to be understood that the first thermoplastic sheet can be also molded to conform to the front of the patient's head (so to the patient's face). The first thermoplastic sheet will conform to the anatomical contours of the front of the patient's head. The immobilization of the head, according to the present invention, can be achieved while the patient is the supine position or in the prone position. This example is illustrated in FIG. 17 wherein a side view of the assembly comprising the support fixation surface 7, the device 1 and the cured thermoplastic sheets 11, 11' is shown. The entire head of the patient in prone position is covered by the double shell mask of the present invention.

For treatment of the patient's head in the prone position, it is also possible to mold the first thermoplastic sheet to conform the back of patient's head while the second sheet is used to conform the front of the patient's head, so the patient's face. After obtaining the sheets in their final state, the patient is placed in the prone position and the sheets are mounted and fixed to the flanged support member such as to conform said prone position of the patient.

In some case, for treatment of a patient in prone position, the device and system of the present invention can be used such as to first mold and cure a thermoplastic sheet on the patient's front head while the patient is in supine position. Afterwards, the cured first thermoplastic sheet is then used to position the patient in the prone position. A second thermoplastic sheet is then molded and cured on the patient's rear head.

In another preferred embodiment, the system, the device and the method of the invention are suitable for immobilizing the head and the neck and the trunk of a patient. In a preferred embodiment, the trunk is at least partially immobilized by the present invention. The system of this embodiment comprises a first moldable thermoplastic sheet, a second moldable thermoplastic sheet and a flanged support member suitable to be mounted to a fixation surface at a distance (d, not shown) from said fixation surface and adapted to receive and retain said first and second moldable thermoplastic sheets. This embodiment is illustrated by FIG. 18 to FIG. 28 which are hereunder described in details.

Figure 26:
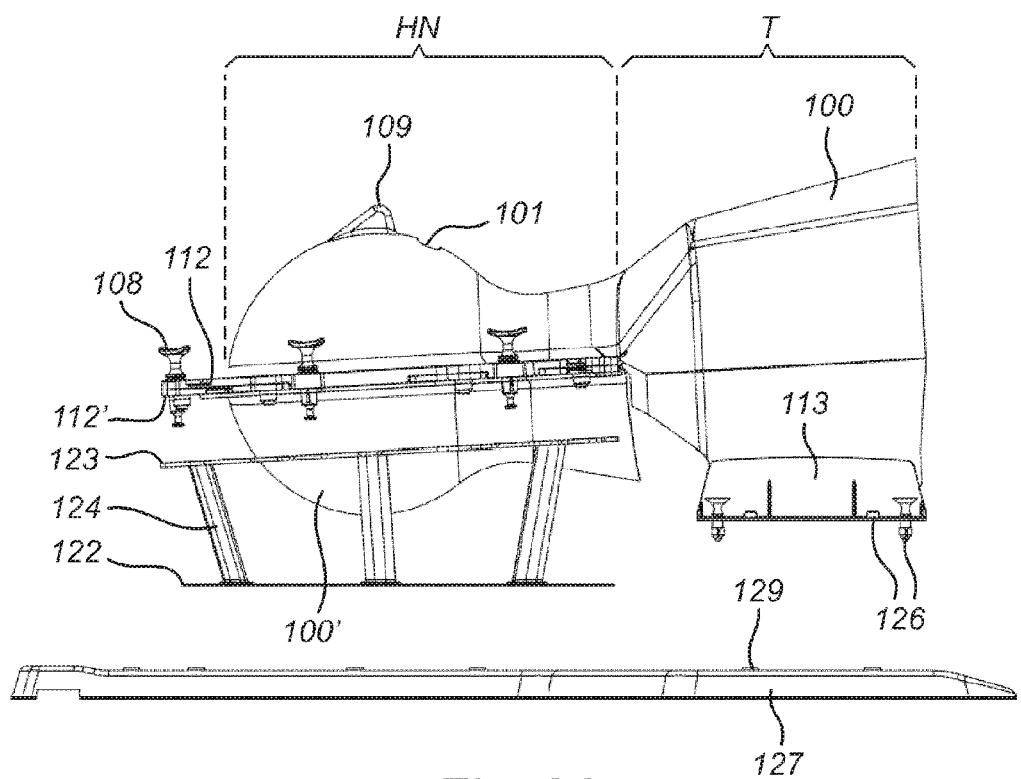
FIG. 26 shows an exploded side view of the fixation surface, the device and the double shell mask for immobilizing a head, a neck and at least part of a patient's trunk according to an embodiment of the invention.

In this embodiment, a device is also provided. Said device might be similar to the first sheet described above for the previous embodiment and might be provided with all the features of the first sheet shown in FIG. 1 to FIG. 17. In a preferred embodiment, the device comprises a bottom plate 122 and a flanged support member 123 adapted to receive and retain at least two moldable thermoplastic sheets. Preferably flanged support member 123 is provided with attachment means 125 for receiving and retaining said thermoplastic sheets. Said bottom plate 122 and flanged support member 123 are connected by an open structure, preferably comprising a plurality of upstanding circumferential support legs 124 (FIG. 26). In a preferred embodiment, the device is suitable to receive and retain a first moldable thermoplastic sheet 100; and a second moldable thermoplastic sheet 100'. In a preferred embodiment, the first and the second moldable thermoplastic sheets 100, 100' are designed to be superimposable.

Figure 18:
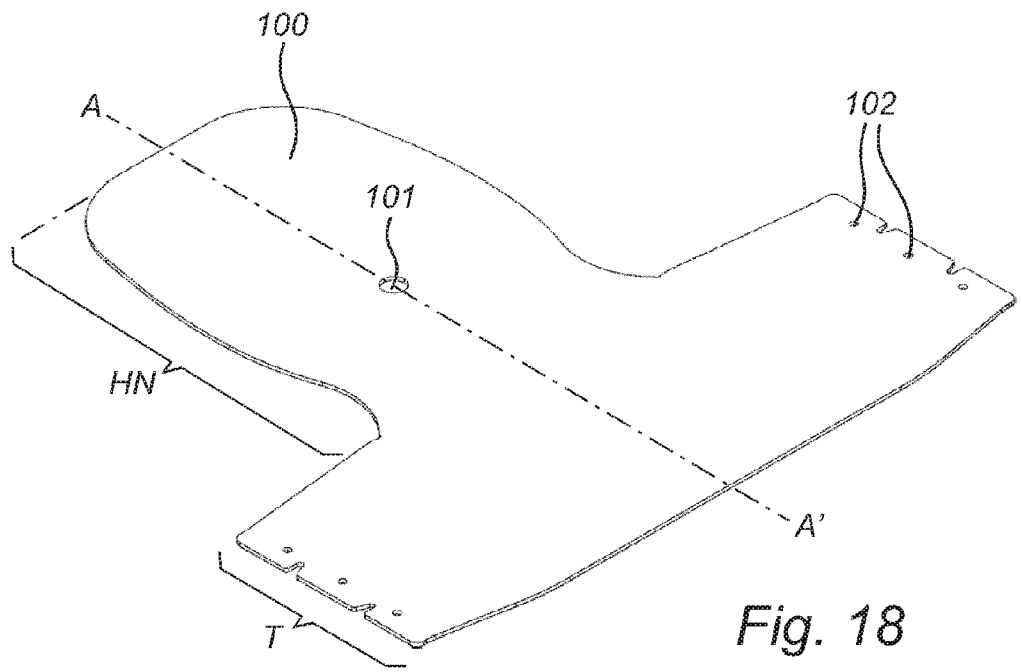
FIG. 18 shows an embodiment of a thermoplastic sheet designed for immobilizing a head, a neck and at least part of a patient's trunk.

In a preferred embodiment, the first and the second moldable thermoplastic sheets 11, 11' comprise each a circumferential rim 112, 112' having a number of connection means 108, 108'. In a further preferred embodiment, the circumferential rims 112, 112' of the first and the second moldable thermoplastic sheets 100, 100' are designed to be superimposable (FIG. 4). In a preferred embodiment, at least one of said thermoplastic sheets is provided with at least one opening 101 for the patient's month as shown in FIG. 18. In another embodiment, both sheets are devoid of openings.

FIG. 18 shows the second moldable thermoplastic sheet 100 comprising an area HN designed to be molded and to cover a first area of the head and the neck of a patient and an area T designed to be molded and to cover a first area of the trunk of a patient. Said sheet is provided with apertures 102 for mounting attachment edges 113 to the sheet 100. Preferably said apertures 102 are provided at the area T designed to be molded and to cover a first area of the trunk of a patient of the sheet 100. Preferably said apertures 102 are provides on either side, i.e. on the left and on the right, of the longitudinal central axis A-A' of the sheet (FIG. 18). The sheet might be provided with one or more openings 101 which might correspond to the mouth or the nose of the patient.

Figure 19:
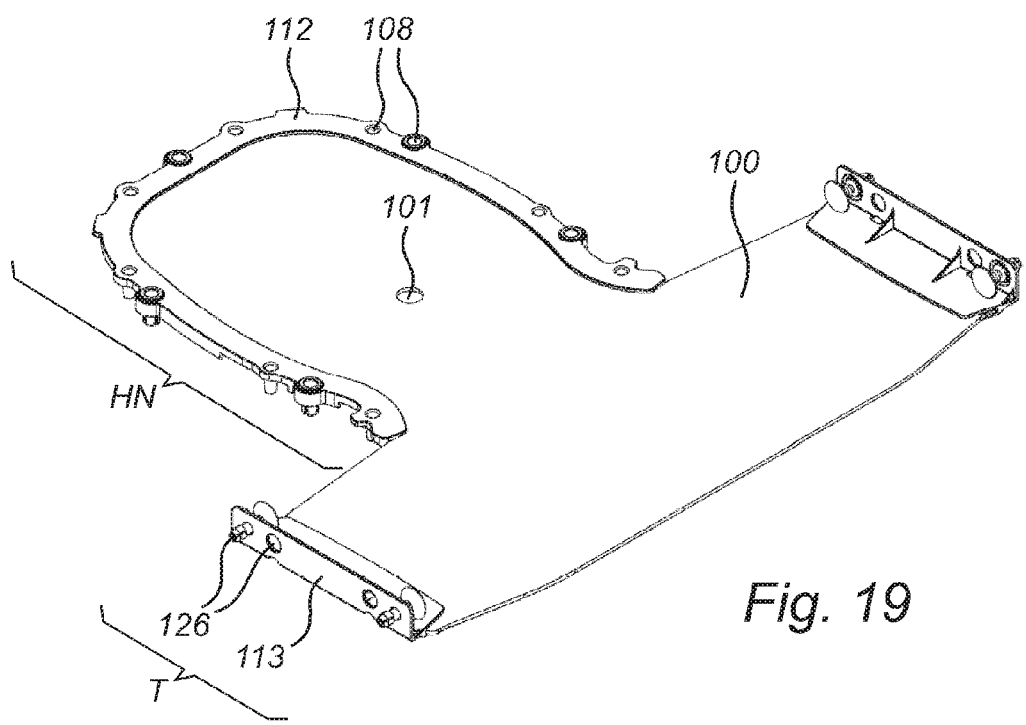
FIG. 19 shows the thermoplastic sheet of FIG. 18 provided with circumferential rim and attachment edges.

In a preferred embodiment, the area HN, designed to be molded and to cover a first area of the head and the neck of a patient, is connectable to a circumferential rim 112 (FIG. 19). The area T, designed to be molded and to cover a first area of the trunk of a patient, is connectable to attachments edges 113 via the aperture 102 (FIG. 19). In a preferred embodiment, the circumferential rim 112 and/or the attachment edges 113 of the moldable thermoplastic sheet 100 are provided with a number of connection means 108.

Figure 20:
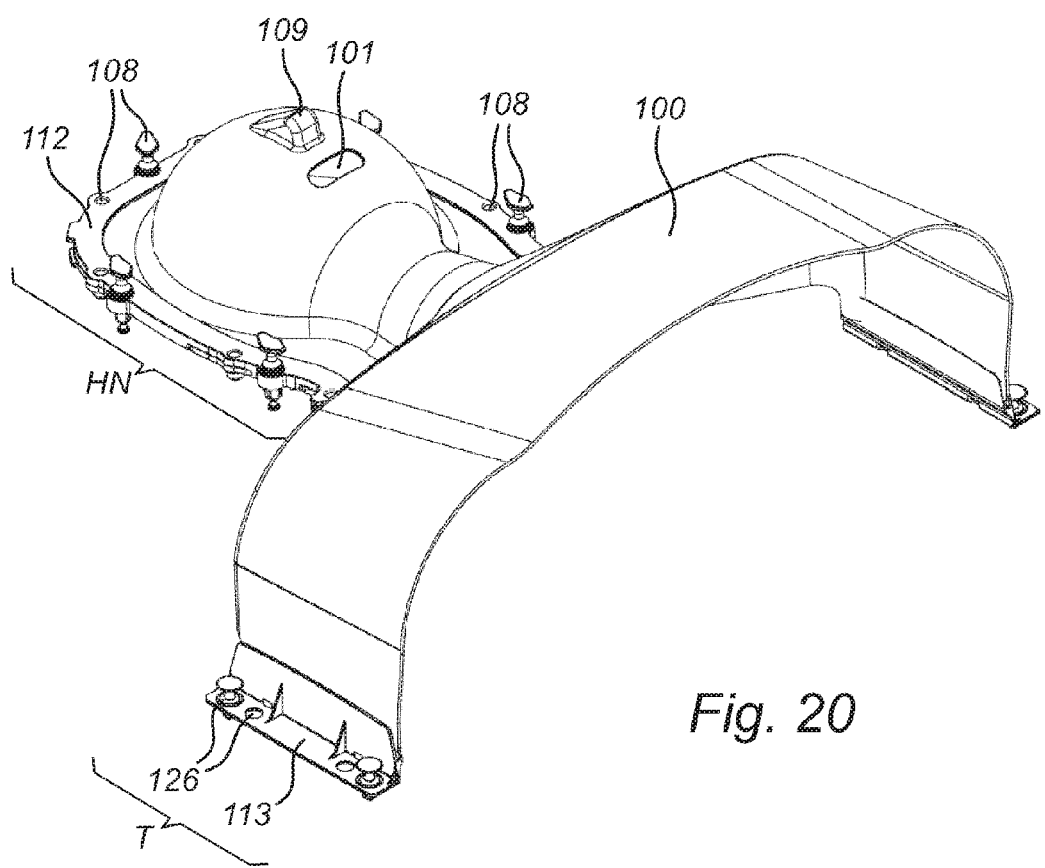
FIG. 20 shows the thermoplastic sheet of FIG. 18 in final state, after molding on a patient's body part and curing.

The second moldable sheet 100 of FIG. 19 is heated and molded on a patient's body part comprising the face, the neck and at least partially the trunk. The sheet will conform and cover the anatomical contours of the patient's body part. After curing, a molded sheet is obtained as shown in FIG. 20. The sheet shows a protrusion 109 corresponding to the nose of the patient and an opening 101 for the mouth of said patient. It is to be understood that the sheet can be also designed to cover the side of the patient comprising the rear head, the rear neck and the back of the patient. The sheet can also be of any other shape and can be designed to cover any body part of a patient.

The present invention also provides a first moldable thermoplastic sheet designed to be molded and to cover an area of the head and the neck of a patient which is not covered by the second moldable thermoplastic sheet. Said first moldable thermoplastic sheet might be similar to the first sheet described above for the previous embodiment and might be provided with all the features of the first sheet shown in FIG. 1 to FIG. 17.

In a preferred embodiment, the first moldable thermoplastic sheet is provided with a circumferential rim 112'. Said circumferential rim 112' can be permanently fixed to the moldable thermoplastic sheets or can be dismountably fixed to said sheet. The latter configuration is advantageous as it allows optimizing the cleaning of the sheets both in their initial and final state. Furthermore, dismountable circumferential rims can be easily changed by new rims if required, for instance if the rim is damaged.

In a preferred embodiment, the circumferential rims 112, 112' of the first and the second moldable thermoplastic sheets 100, 100' are each provided with a number of connection means 108, 108'. In a further preferred embodiment, the circumferential rims 112, 112' of the first and the second moldable thermoplastic sheets 100, 100' are designed to be superimposable.

In a preferred embodiment, the connection means 108, 108' of thermoplastic sheets circumferential rims 112, 112' are selected from the group comprising: rivets, screws, bolts and nuts, and snap fit means connections or any other type of connections means known to the person skilled in the art. The connection means 108, 108' can also be simply openings wherein a fastening means such as rivets or bolts can be introduced and used. In a preferred embodiment, each circumferential rim is provided with 3 to 30, preferably 5 to 25, more preferably 10 to 20 connection means.

In a preferred embodiment, the connection means 108 of the circumferential rim 112 of the first thermoplastic sheet 100 are positioned such as to correspond to all or to a part the connection means 108' of the circumferential rim 112' of the second thermoplastic sheet 100' and/or to all or to a part of the attachment means 125 of the flanged support member 123 of the device when the first and the second thermoplastic sheets are simultaneously attached to the flanged support member 123.

In a preferred embodiment, the connection means 108' of the circumferential rim 112' of the second thermoplastic sheet 100' are positioned such as to correspond to all or to a part of the connection means 108 of the circumferential rim 112 of the first thermoplastic sheet 100' and/or to all or to a part of the attachment means 125 of the flanged support member 123 of the device when the first and the second thermoplastic sheets are simultaneously attached to the flanged support member 123.

In a preferred embodiment, the connection means 108, 108' are positioned on the circumferential rims 112, 112' such as to correspond intermittently with all or with a part of the attachment means 125 of the flanged support member 123. For instance, each attachment means 125 of the flanged support member 123 corresponding with a connection means 108 of the first thermoplastic sheet 100 will have a left and right neighboring attachment means that correspond with two connection means 108' of the second thermoplastic sheet 100'. Similarly, each attachment means 125 of the flanged support member 123 corresponding with a connection means 108' of the second thermoplastic sheet 100' will have a left and right neighboring attachment means that correspond with two connection means 108 of the first thermoplastic sheet 100.

Figure 21:
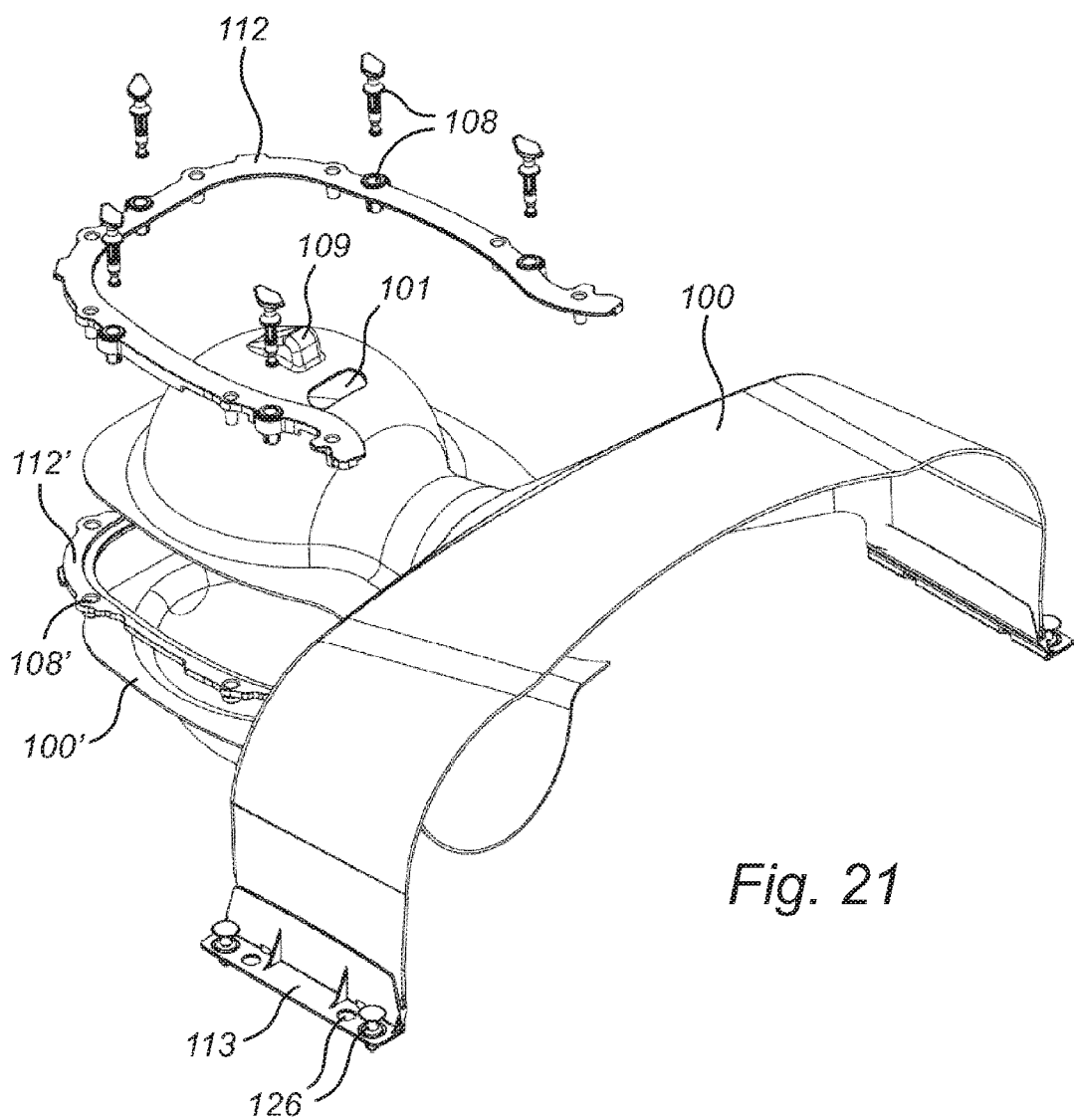
FIG. 21 shows an exploded view of an embodiment of the double shell mask for immobilizing a head, a neck and at least part of a patient's trunk. The mask comprises the molded thermoplastic sheets wherein one sheet is provided with attachment edges and the circumferential rims of the sheets.
Figure 22:
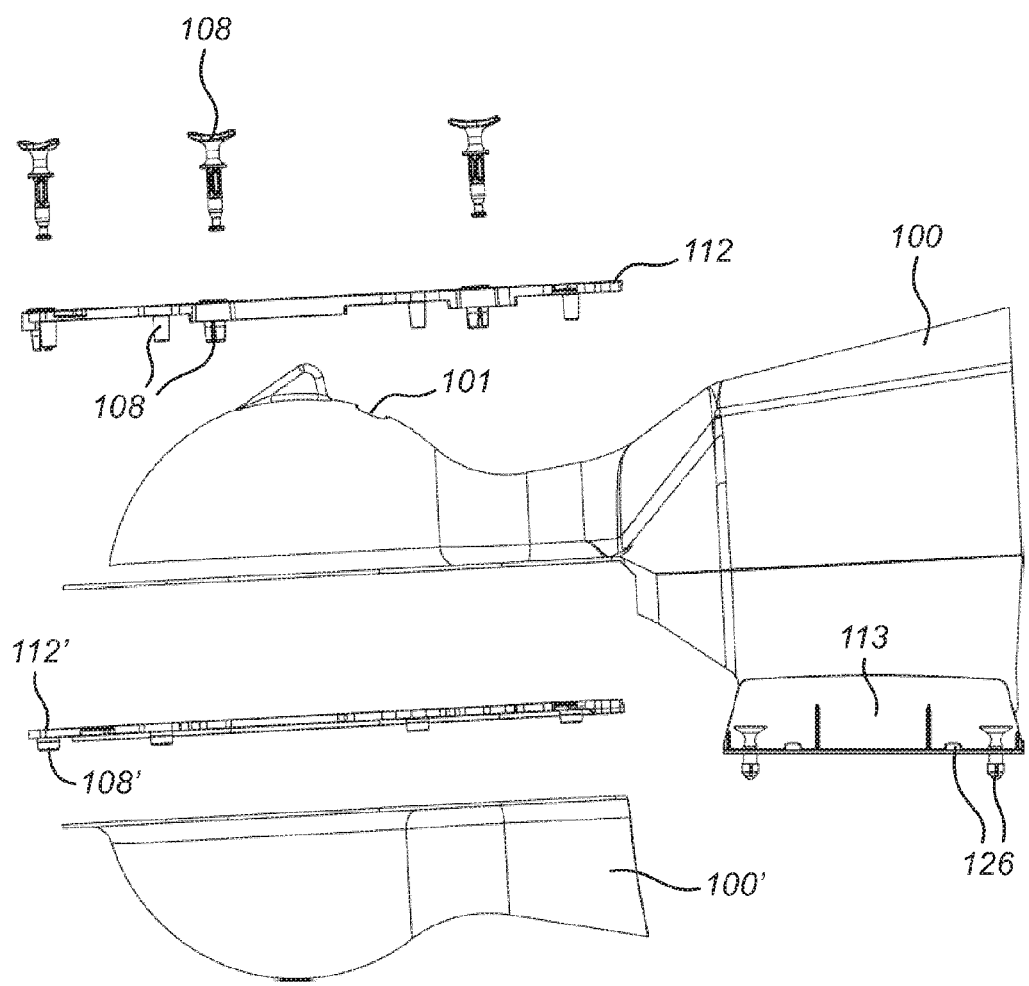
FIG. 22 shows an exploded side view of the double shell mask for immobilizing a head, a neck and at least part of a patient's trunk. The mask comprises the molded thermoplastic sheets wherein one sheet is provided with attachment edges and the circumferential rims of the sheets.

FIG. 21 shows an exploded view of the double shell mask according to an embodiment of the invention. Said double shell mask comprises the first and the second thermoplastic sheets 100, 100' in a molded state. The figure also shows the respective rims 112, 112' and the connection means 108, 108'. The first molded thermoplastic sheet 100 is designed to cover and to conform the anatomical contours of the face, the neck and at least partially the trunk of a patient. FIG. 22 shows an exploded side view of the double shell mask according to an embodiment of the invention and presented in FIG. 21.

Figure 23:
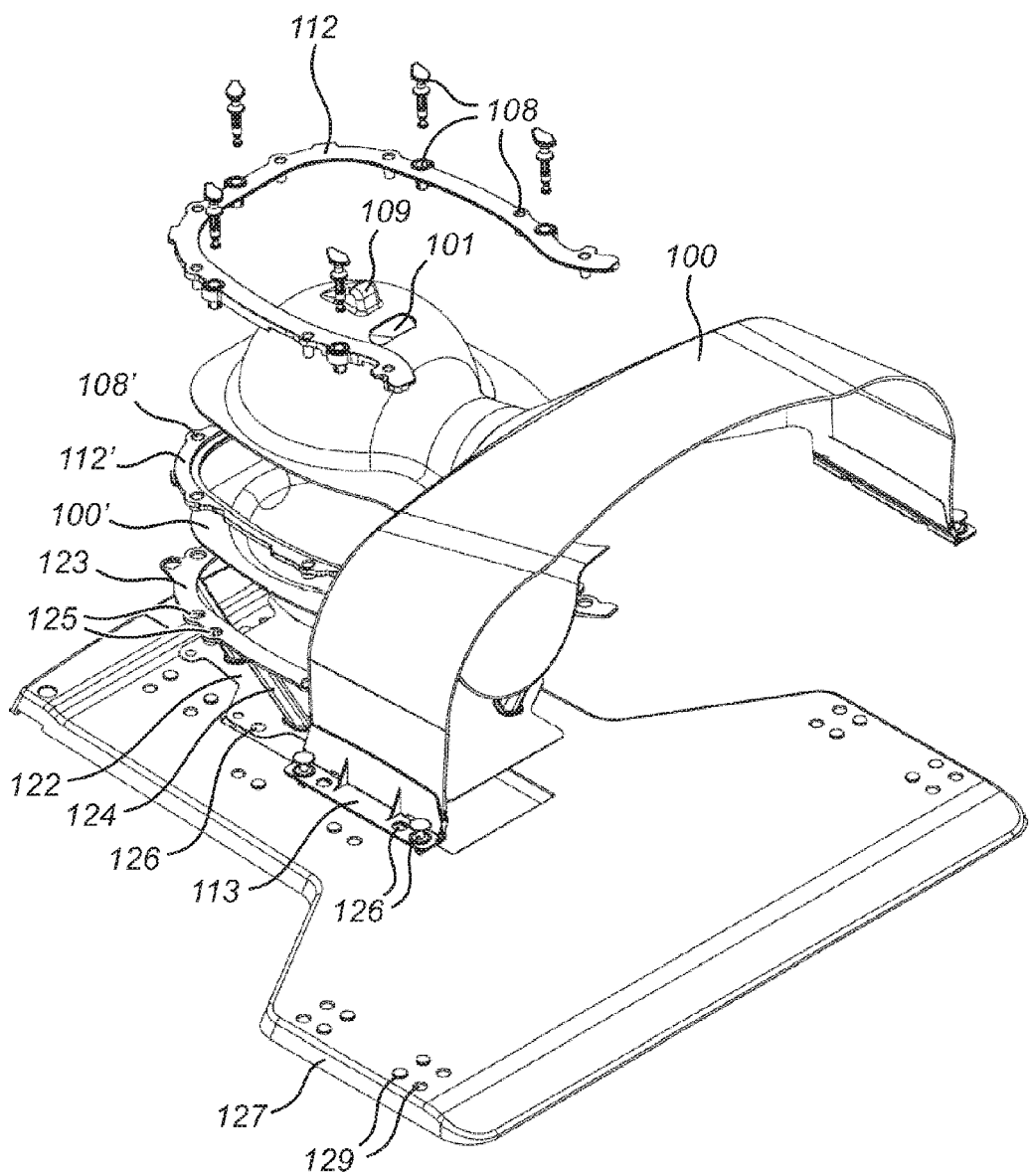
FIG. 23 shows an exploded view of the support fixation surface, the device, the moldable thermoplastic sheets and their respective circumferential rims for immobilizing a head, a neck and at least part of a patient's trunk according to an embodiment of the invention.
Figure 24:
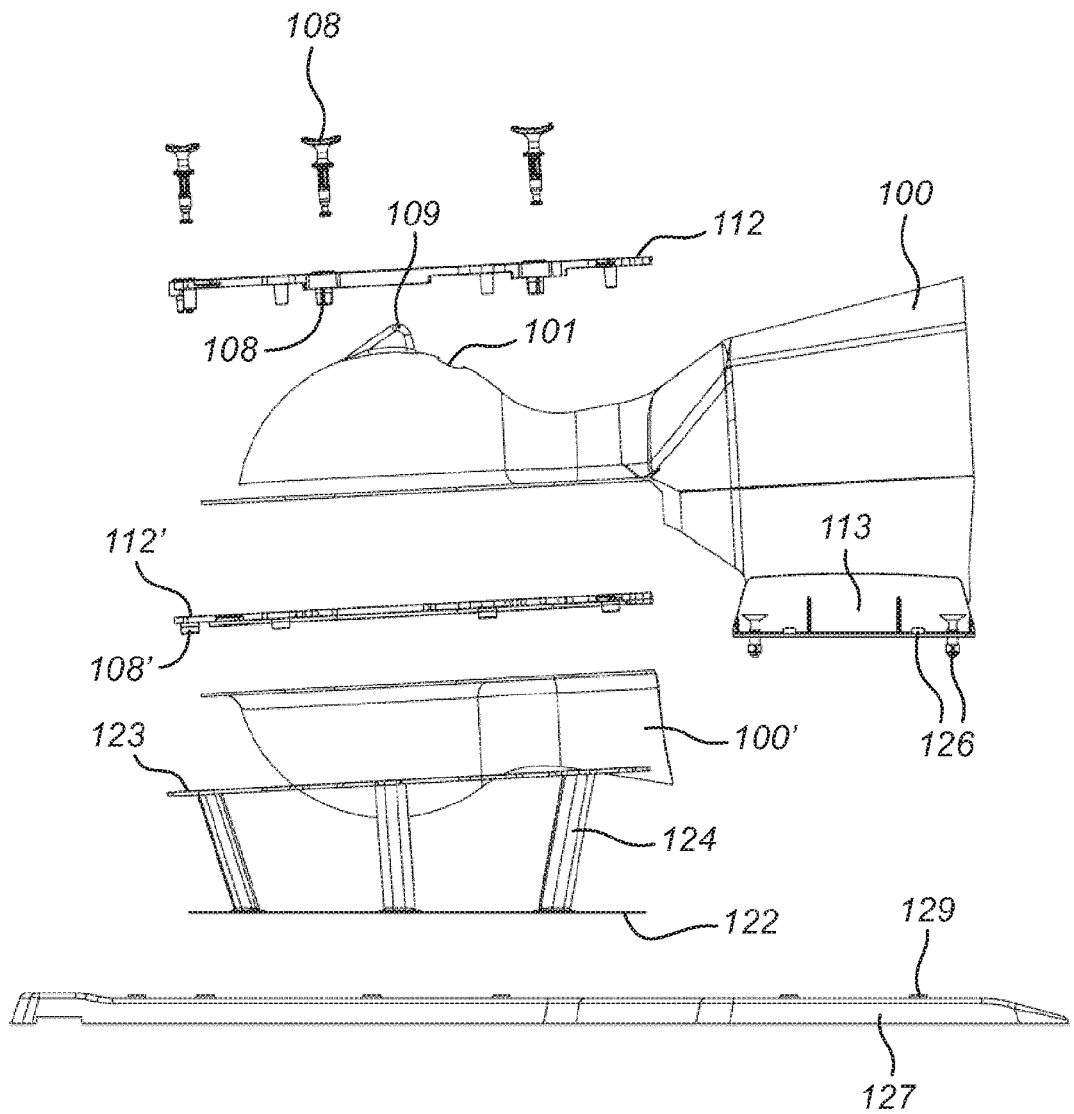
FIG. 24 shows an exploded side view of the support fixation surface, the device, the moldable thermoplastic sheets and their respective circumferential rims for immobilizing a head, a neck and at least part of a patient's trunk according to an embodiment of the invention.

FIG. 23 and FIG. 24 show respectively an exploded view and a side exploded view of the double shell mask, the device and the fixation surface according to an embodiment of the invention. The device is suitable to be mounted to the fixation surface 127 using support surface fixation means 129 which correspond to fixation means 126 provided on the bottom plate of the device (FIG. 3). In a preferred embodiment, the attachment edges 113 of the second moldable sheet 100 are also provided with fixation means 126 for fixing the sheet 100 area T, designed to be molded and to cover a first area of the trunk of a patient, to the fixation surface 127.

Preferably, the support surface fixation means 129 of the fixation surface 7 correspond to fixation means 126 of the bottom plate. The fixation means of the bottom plate and the corresponding fixation means of the support fixation surface are selected from the group comprising: rivets, screws, bolts and nuts, and snap fit means connections and foam or plastic pads or parts that will fit in recesses in the support fixation surface or baseplate. Preferably, the fixation means 126 of the bottom plate 122 comprise snap fit connections and rivets. More preferably, said provided snap fit connections and rivets are provided in an intermittent pattern. In a preferred embodiment, the bottom plate is provided with 3 to 30, preferably 5 to 25, more preferably 10 to 20 fixation means.

Figure 25:
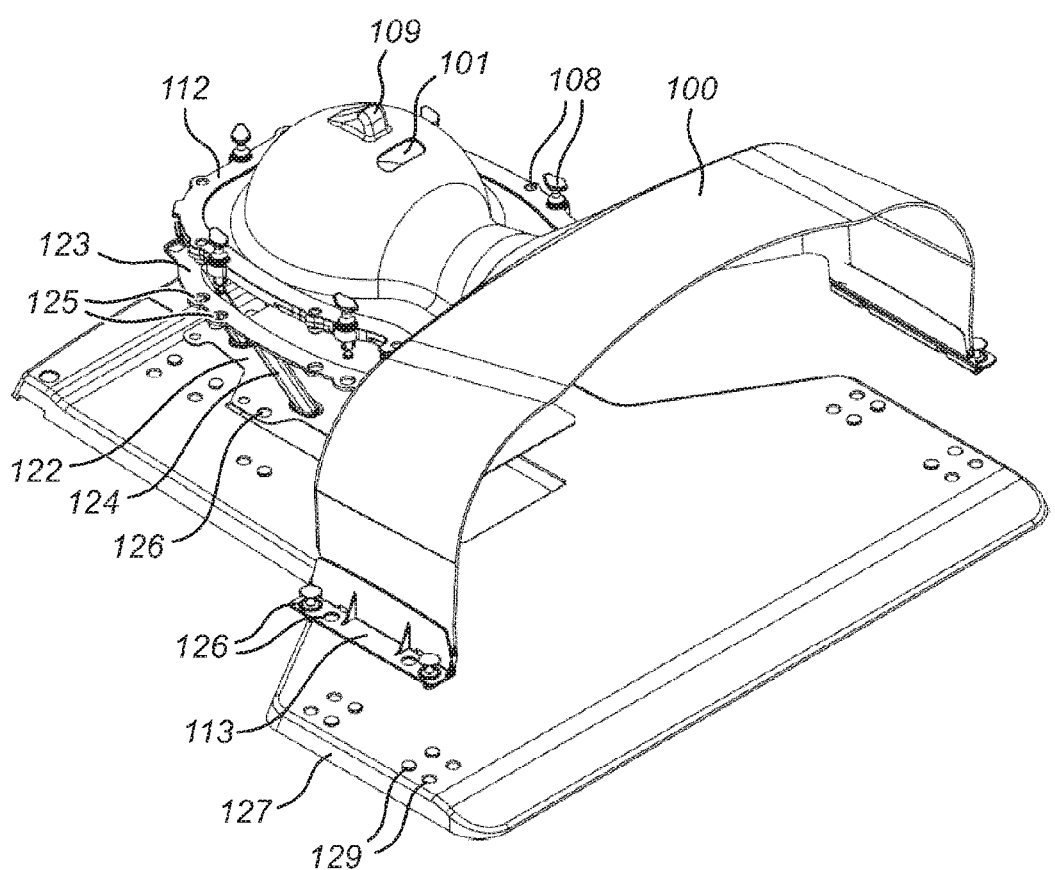
FIG. 25 shows an exploded view of the fixation surface, the device and the double shell mask for immobilizing a head, a neck and at least part of a patient's trunk according to an embodiment of the invention.

FIG. 25 shows the double shell mask comprising the molded thermoplastic sheets 100, 100' and the rims 112, 122' fixed to each other. Said mask is suitable to be attached to the flanged support member 123 of the device via the rims 122, 122' using the connection means 108, 108'. Said device is suitable to be fixed to the fixation surface 127, FIG. 24 shows a side view of the mask, the device and the fixation surface shown in FIG. 26.

Figure 27:
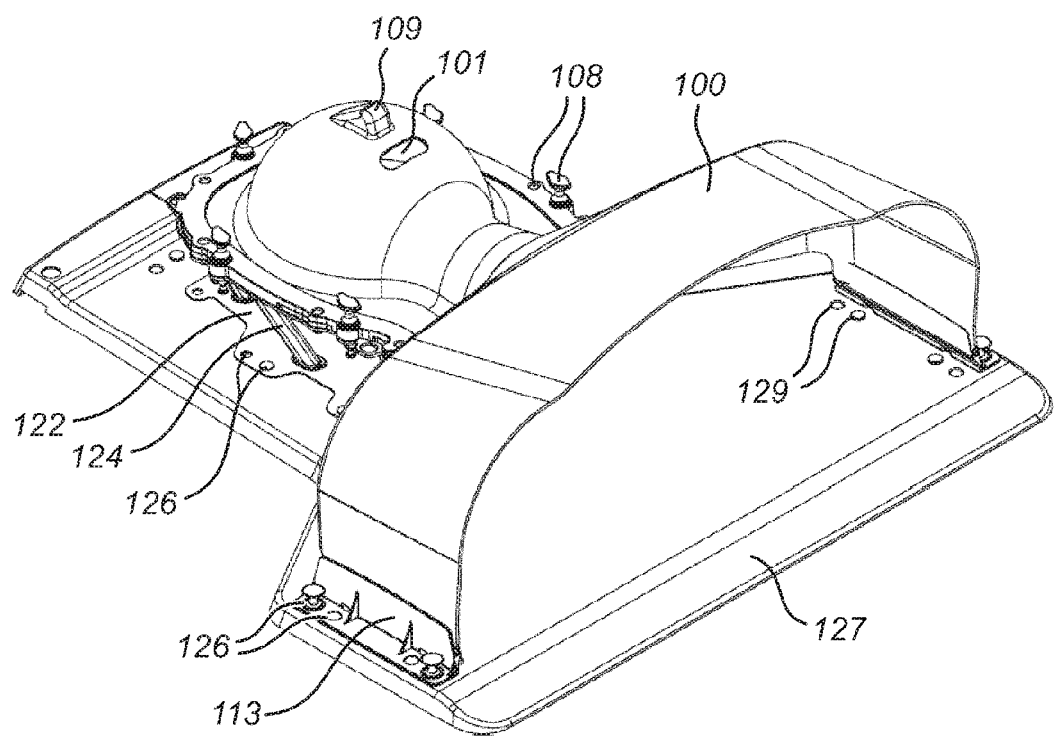
FIG. 27 shows a perspective of an embodiment of the device to which the double shell mask is fixed. The device and the mask are fixed to a fixation surface.

FIG. 27 shows the double shell mask comprising the molded thermoplastic sheets 100, 100' and the rims 112, 122' fixed to each other. Said mask is attached to the flanged support member 123 of the device via the rims 122, 122' using the connection means 108, 108'. The device is itself fixed to the fixation surface 127 using the support surface fixation means 129 of the fixation surface 127 and the fixation means 126 of the bottom plate of the device. The attachment edges 113 of the second moldable sheet 100 are also fixed to the fixation surface using the fixation means 126 of said attachment edges 113, thereby fixing the sheet area T, designed to be molded and to cover a first area of the trunk of a patient, to the fixation surface 127. In a preferred embodiment, the fixation surface 127 is provided with fixation means 129 positioned such as to correspond to different body and more in particular to different trunk widths including the left and the right arms of the patient.

Figure 28:
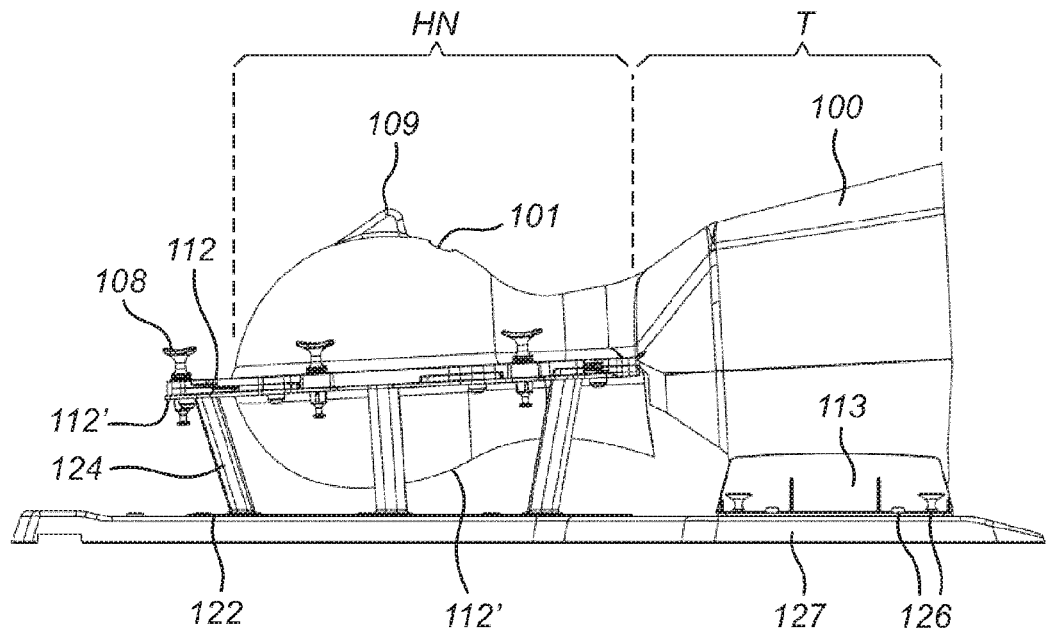
FIG. 28 shows a side view of an embodiment of the device to which the double shell mask is fixed. The device and the mask are fixed to a support fixation surface.
Figure 28A:
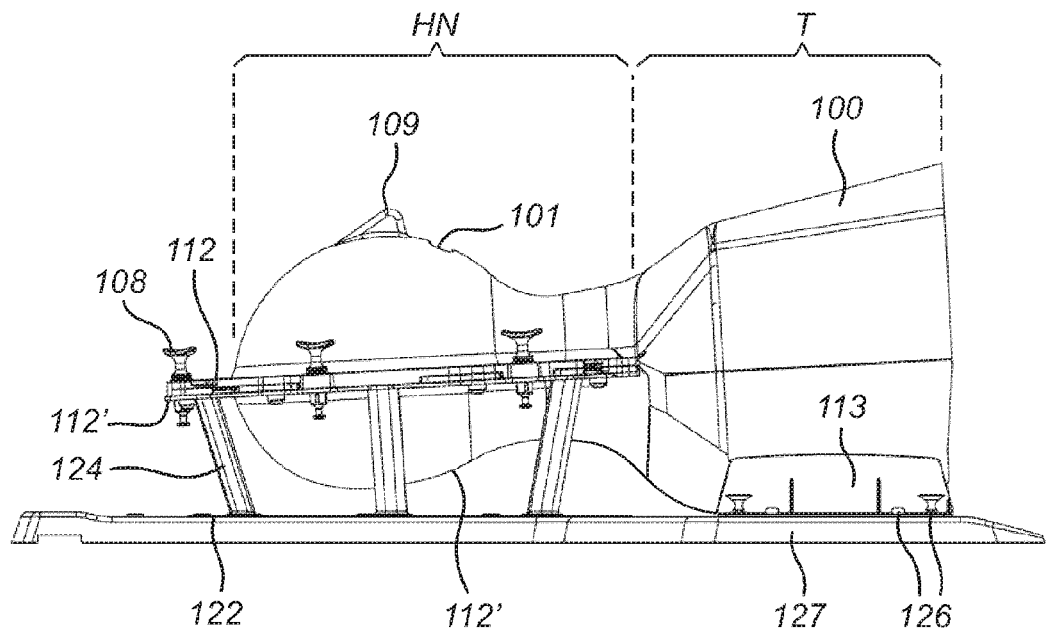
FIG. 28A shows a side view of an embodiment of the device to which the double shell mask is fixed. The device and the mask are fixed to a support fixation surface. The double shell mask is covering the head, the neck and at least part of the patient's trunk.

FIG. 28 shows a side view of the mask, the device and the fixation surface shown in FIG. 27.

FIG. 23 to FIG. 28 show that the rims 112, 112' are superimposable and that said rims are also at least partially superimposable with the flanged support member 123. The mentioned figures shows the different steps for immobilizing patient body par using the system, the devices and the method of the invention. Although a patient is not shown in the figures, it is to be understood that for a first use, the moldable sheets are in their initial state. The first sheet is fixed to the flanged support member via its rim. Said flanged support member is already mounted on the fixation surface. Said first sheet is heated before or after fixing it on to the flanged support member. The patient body part to be immobilized is placed on the first sheet which will deform and conform the anatomical contours of the body part thereby covering a first area of said body part. The second sheet is then heated and fixed to the flanged support member via its rim. The second sheet will then deform and conform the anatomical contours of the body part thereby covering a second area of the body part which is not covered by the first sheet. After treatment, the molded sheets can be dismounted from the flanged support member and stored for a personalized future use.

The patient's body part immobilized using the system, method and/or device according to any embodiment of the present invention is immobilized in a free floating manner. This refers to the fact that said body part is only supported by the thermoplastic sheet and the flanged support member. The body part is immobilized in a way which is devoid of any support cushion or support material. A free space is hence available between the immobilized body part and the fixation surface of the device thereby providing a 360° C. free access of the practitioner to the immobilized body part.

In a preferred embodiment, the system according to the present invention further comprises stabilization means for optimizing the immobilization of the patient's body part. For treatments comprising the application of radiations to a specific zone of the immobilized body part, it is highly recommended to avoid any movement of said body part during the treatment. Also for repetitive treatments comprising the application of radiations to a specific zone of the immobilized body part, it is crucial to exactly reproduce the immobilization position of said body part during each application of the radiations. This leads to an enhancement of the efficacy of the treatment and avoids application of radiations to zones of the immobilized body part surrounding the specific zone to be treated. Such treatments can be spread over a long time which can be from few weeks to few months. It is often the case that the positioning of the immobilized body part is not reproduced with exactitude. This might be due, for instance, to slight modifications of the orientation of the body part to be immobilized during each treatment and/or to small weight loss of the patient. The stabilization means provided by the present invention are advantageous as they allow the exact reproduction of the immobilization position during repetitive treatment of the immobilized body part. The stabilization means further improve said immobilization and serve as marks to exactly reproduce the immobilization position during repetitive treatment.

In a preferred embodiment, the stabilization means are dismountably fixed to the flanged support member and/or to at least one of the rims of the thermoplastic sheets for optimizing the immobilization of said body part. Preferably, said stabilization means comprise at least one stabilization means support and at least one stabilization device. Preferably, the stabilization means are suitable to be dismountably fixed to the flanged support member and/or to at least one of the rims of the thermoplastic sheets via said stabilization means support.

Figure 29:
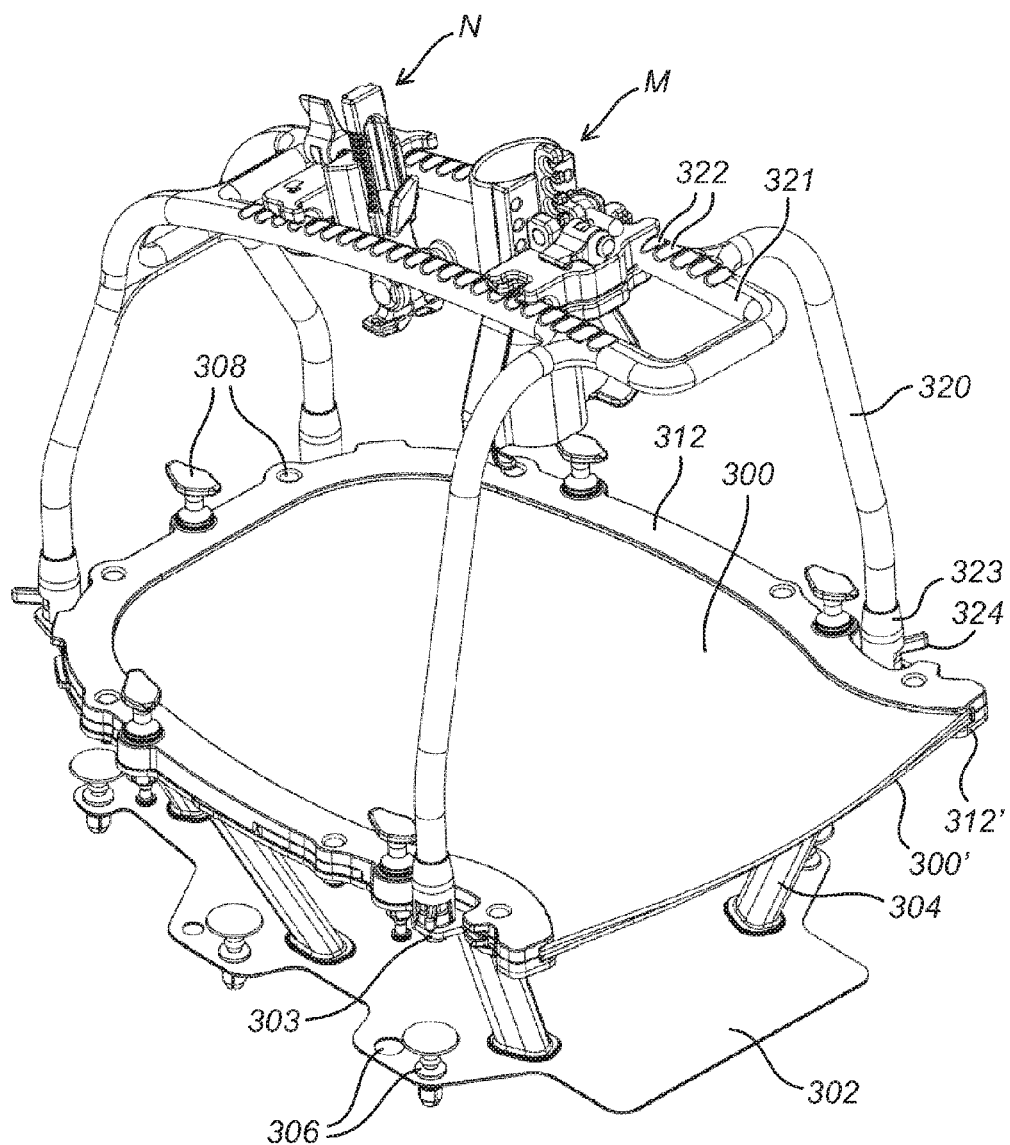
FIG. 29 shows a perspective view of the device and the thermoplastic sheets to which stabilization means is attached and fixed.
Figure 30:
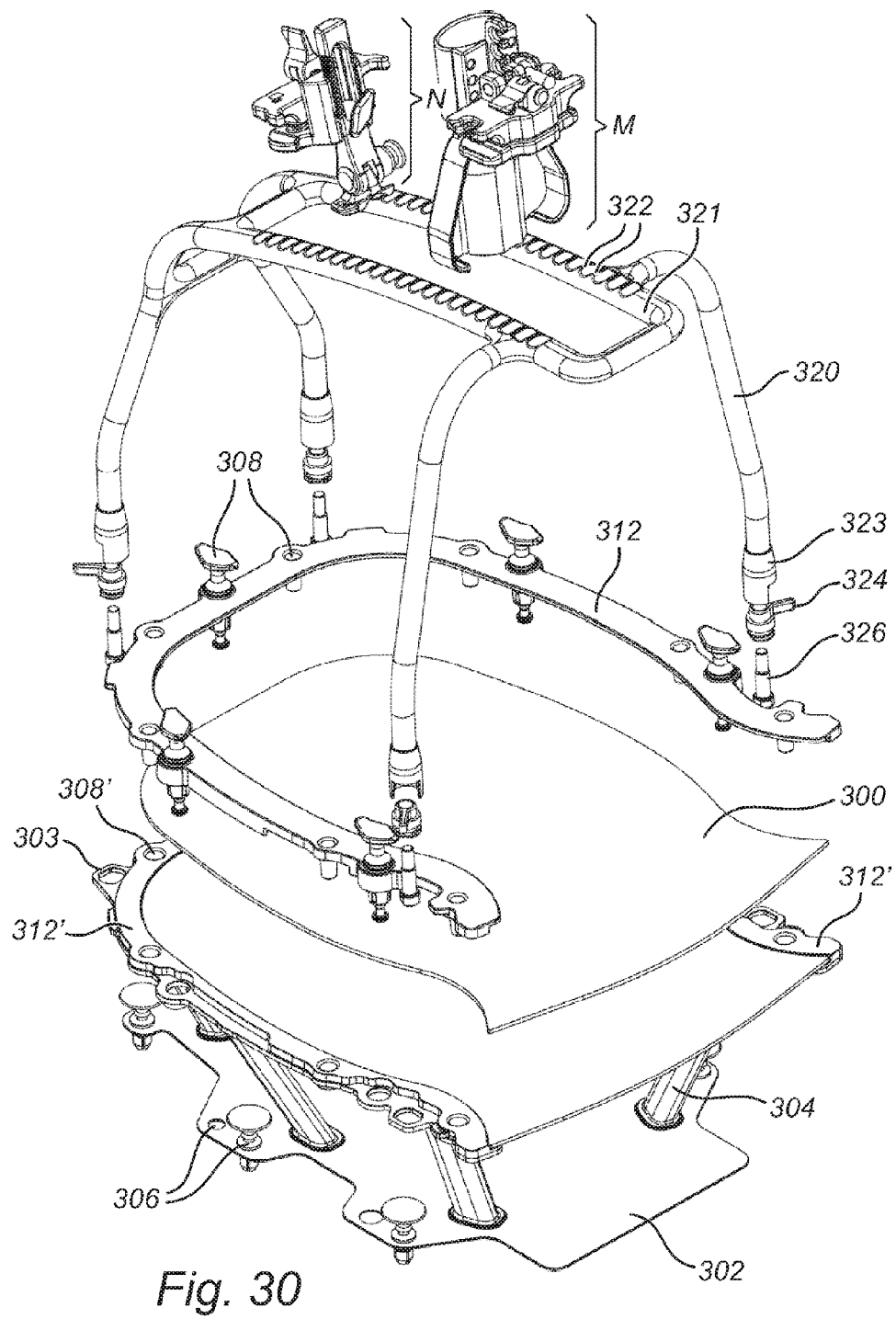
FIG. 30 shows an exploded view of the device, the thermoplastic sheets and the stabilization means of FIG. 29.

FIG. 29 and FIG. 30 show respectively a perspective view and an exploded view of the device to which two thermoplastic sheets 300, 300' in their initial state are fixed. The device shown in FIG. 29 and FIG. 30 comprises a bottom plate 302 provided with fixation means 306 for fixing said device to a fixation surface; a flanged support member 303 provided with attachment means 305 for attaching the sheets to the device; and a plurality of upstanding circumferential support legs 304. It is to be understood that the device might comprise the flanged support member 303 and is suitable to be mounted to a fixation surface using support member fixation means, such as said flanged support member is fixed and at a distance d from said fixation surface.

The thermoplastic sheets 300, 300' are each dismountably connected to a rim 312, 312' wherein each rim is provided with connection means 308, 308' for attaching the sheets to the flanged support member 303 of the device (FIG. 29 and FIG. 30). In a preferred embodiment, the connection means 308, 308' of thermoplastic sheets circumferential rims 312, 312' are selected and/or positioned as described above for the embodiments represented by FIG. 1 to FIG. 17 and by FIG. 19 to FIG. 28.

Stabilization means, comprising at least one stabilization means support and at least one stabilization device M, N, is suitable to be fixed and mounted to the flanged support member 303 and/or to at least one of the rims 312, 312' of the thermoplastic sheets 300, 300' (FIG. 29 and FIG. 30). The stabilization means support comprises at least one frame 321 for dismountably holding and fixing at least one stabilization device; said frame 321 is connected to at least one upstanding member 320, preferably to a plurality of upstanding members 320. The upstanding members are releasably connectable to the flanged support member 303 and/or to at least one of the rims 312, 312' of the thermoplastic sheets 300, 300'.

The frame 321 of the stabilization means can be of any shape provided it is suitable to dismountably hold and fix at least one stabilization device. Said frame can have a shape selected from the group comprising square, circular, triangular shape or any other shape. Preferably said frame has a rectangular shape (FIG. 29, FIG. 30 and FIG. 31).

In a preferred embodiment, the frame 321 is provided with a plurality of serrations 322 for fixing the stabilization devices M, N to said frame. Preferably said serrations 322 are provided on at least two parallel opposite sides of the frame 321. The serrations are preferably provided over the full length of said frame sides. This allows fixation of the stabilization devices to the frame at different positions thereby adapting the position of the stabilization devices to the immobilized body part. In the embodiment shown in FIG. 29 and FIG. 30, the device, the sheets and the stabilization means are provided for immobilizing the head of a patient. In this embodiment, two stabilization devices are provided wherein one stabilization device M is designed for the mouth of the patient and the other stabilization device N is designed for the nose of the patient. It is to be understood that the immobilization device can be adapted and designed to immobilize any other body part. Also the stabilization device can be adapted and designed to stabilize any other body part.

Figure 31:
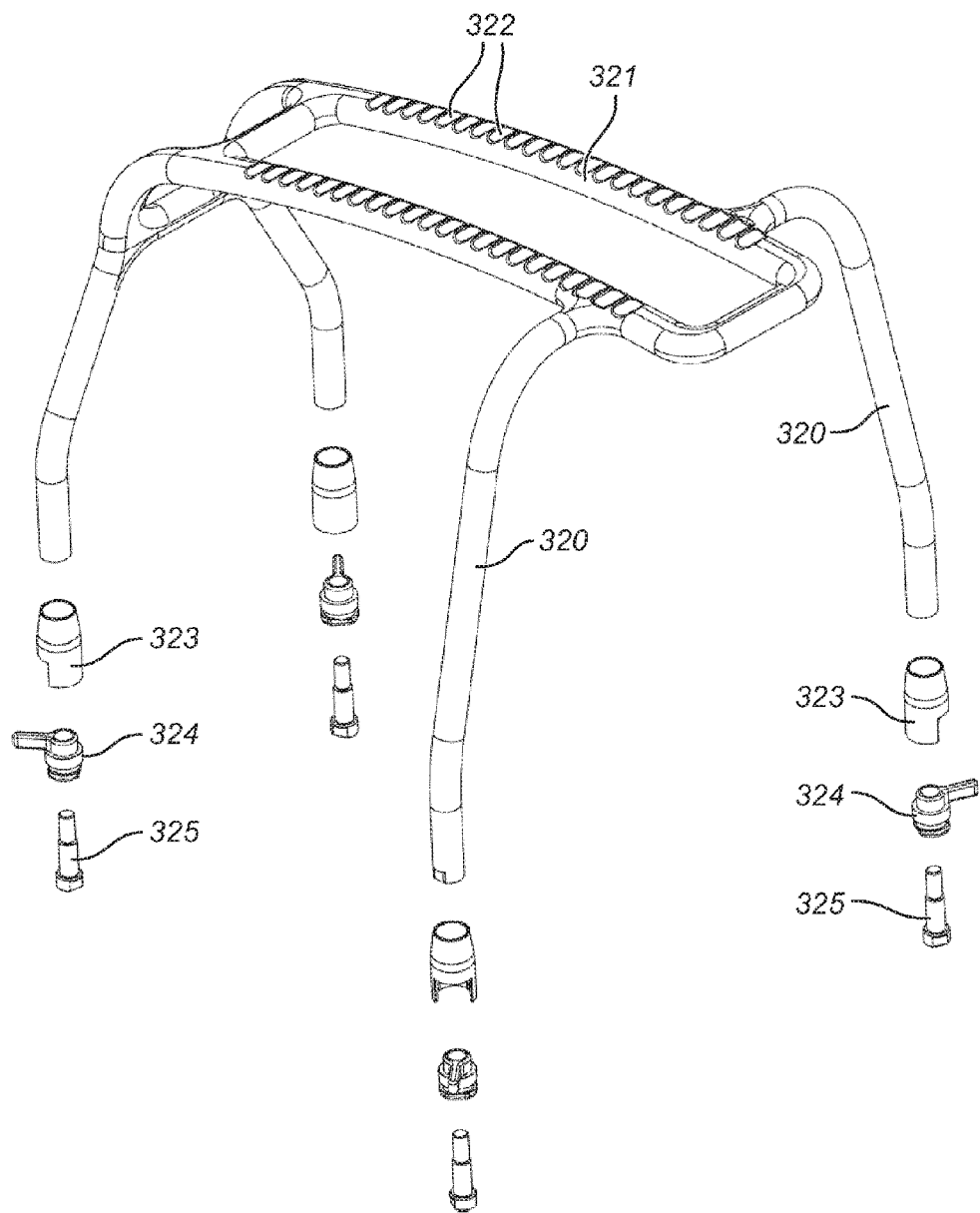
FIG. 31 shows an exploded view of the stabilization means support.

A preferred embodiment of the stabilization means support is shown in FIG. 31. The support comprises frame 321 provided with serrations 322 and comprises a plurality of upstanding member 320 for fixing the stabilization means support at a distance d from the flanged support member 303 and/or at least one of the rims 312, 312' of the thermoplastic sheets 300. The upstanding members are, at one end, permanently or dismountably attached to the frame 321. The distance d is determined by the length of the upstanding members 320. Said upstanding member can be provided with a fixed length or a variable length. By variable length, we refer to the possibility of shortening or making longer the upstanding members.

In a preferred embodiment, the end of the upstanding member 320 which is not attached to the frame 321 is suitable to receive coupling means 323, 324, 235 (FIG. 31) for dismountably fixing the stabilization means support to the flanged support member 303 and/or to at least one of the rims 312, 312' of the thermoplastic sheets 300, 300'. Said coupling means are selected from the group comprising screws, blind, rivets, tacks, nails, nuts, pins, bolts, rivets, clamps, actuated lever clamps or any combination thereof. Preferably said coupling means are actuated lever clamps which are movable between a locked position and unlocked position.

In a preferred embodiment, the stabilization device is dismountably fixed on the frame 321 of the stabilization means support. Said stabilization device comprises at least one fastening means for fastening the stabilization means to the frame 321; at least one positioning means suitable to be in contact with an area of the immobilized patient body part; and adjustment means for changing the position of the positioning means.

In a preferred embodiment, the stabilization device M designed for the mouth is dismountably fixed on the frame 321 of the stabilization means support. Said stabilization device M comprises fastening means 341, 342, 343 for fastening the stabilization means to the frame 321. In a preferred embodiment, the stabilization device M comprises at least one positioning means 327 suitable to be in contact with an area of the immobilized patient body part and adjustment means 340 for changing the position of the positioning means 327, thereby adapting its position to the targeted area of the immobilized body part.

Figure 32:
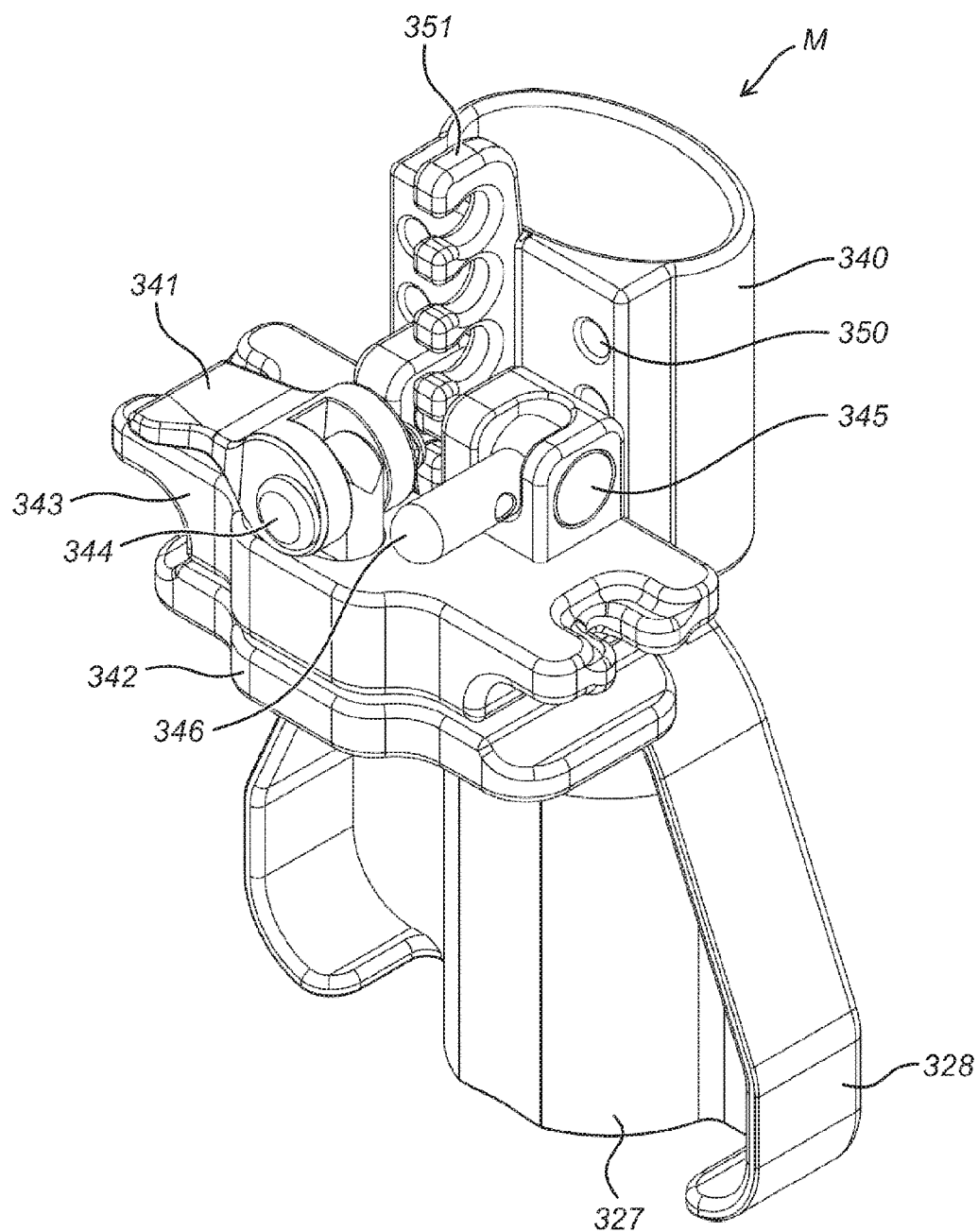
FIG. 32 shows a perspective view of the first stabilization device.
Figure 33:
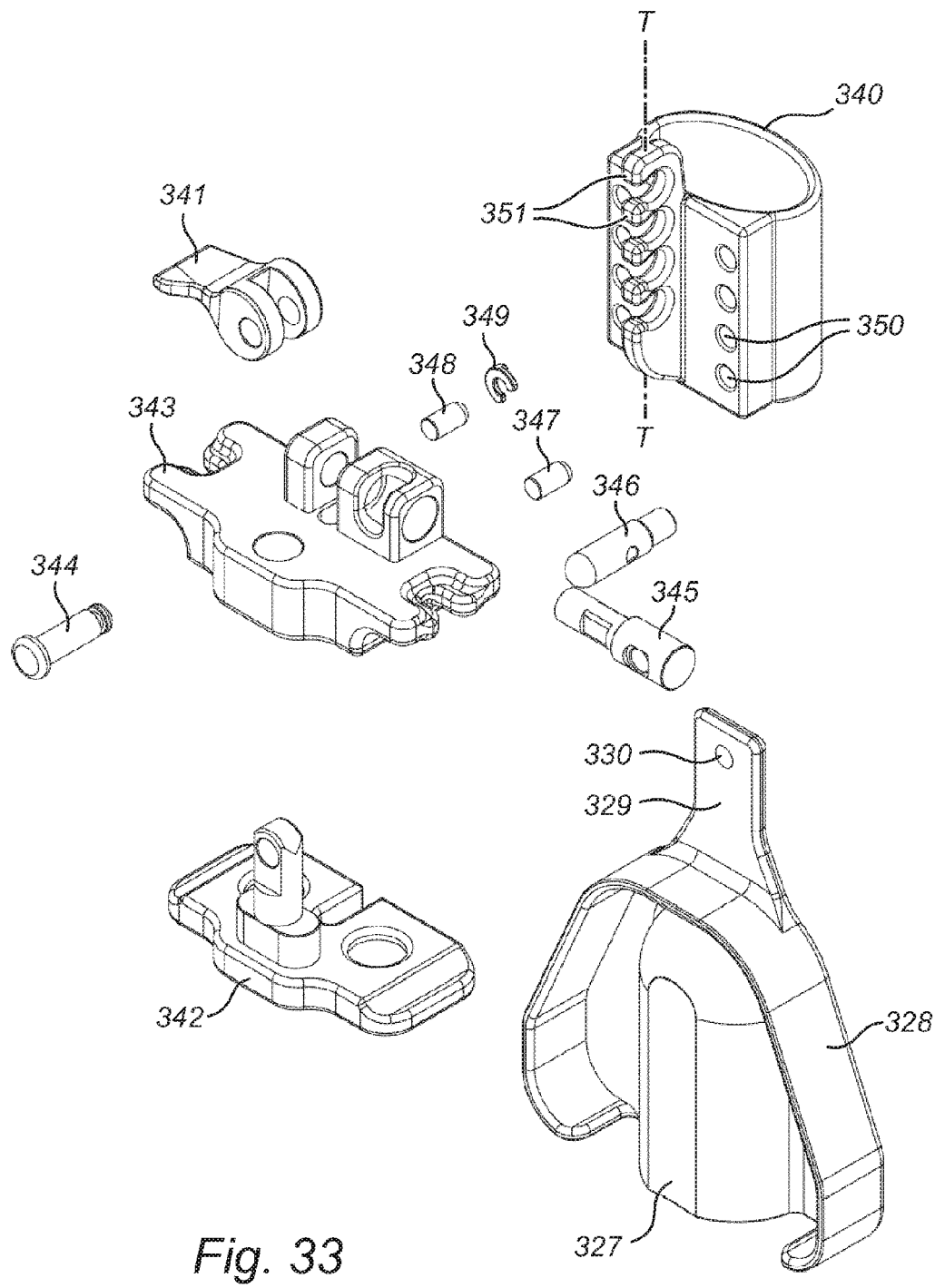
FIG. 33 shows an exploded view of the first stabilization device.

In the embodiment shown in FIG. 32 and FIG. 33, the positioning means 327 is suitable to be in contact with the mouth of the patient and/or to be bitten by the patient. Consequently, optimized and/or complete immobilization of the patient's head during treatment in ensured. The positioning means 327 can be made of silicone, rubber or any other suitable material. The positioning means 327 can be dismountably connected to a covering body 328 and is suitable to be replaced by a new positioning means when required. It is to be understood that the positioning means can be of any other shape and/or any other material.

In a preferred embodiment, the fastening means are components of an actuated lever clamp comprising a lever 341 and at least two clamping jaws 342, 343. The lever 341 is movable between a locked position and an unlocked position. In the locked position, the clamping jaws 342, 343 are at least partially surrounding the edges of the frame 321 and are clamped around said edges thereby fixing the stabilization device to the stabilization means support. In the unlocked position, the clamping jaws 342, 343 are not surrounding the edges of the frame 321 thereby removing the stabilization device from the stabilization means support. Preferably, said clamping jaws 342, 343 are designed to form-fit the serrations 322 of the frame 321. Hence, the user controls the position of the stabilization device M on the frame and thereby the position of the stabilization device with respect to the immobilized body part.

In a preferred embodiment, the positioning means 327 is dismountably connectable to the adjustment means 340 which comprises a plurality of hook like attachment means 351 suitable for receiving and/or fixing the positioning means and/or the fastening means. The adjustment means 340 further comprises openings 350 for receiving and/or fixing the positioning means and/or the fastening means. The positioning means 327 and/or the covering body 328 is provided with a connection plate 329 comprising at least one opening 330 for connecting said positioning means to the adjustment means (FIG. 32 and FIG. 33).

The exploded view of the stabilization device M provided in FIG. 33 shows the different components of the fastening means, i.e. the lever 341 the clamping jaws 342, 343. The same figure further shows the positioning means 327, the adjustment means 340 and the different means 344, 345, 346, 347, 348, 349 used for assembling said components. Said means are selected from the group comprising screws, blind, rivets, tacks, nails, nuts, pins, bolts, rivets or any combination thereof. When assembled as shown in FIG. 32, the user can easily dismount the adjustment means 340 from the stabilization device M. The user can then select the position of the positioning means 327 with respect to the adjustment means 340 by selecting one hook like attachment means 351 for attaching the adjustment means 340 to the stabilization device M. Preferably, the hook like attachment means 351 are positioned on the adjustment means 340 such as to define a translation direction T-T of the positioning means 327 (FIG. 33).

For attaching the stabilization device M to the frame 321 of the stabilization means support as shown in FIG. 29, the user or practitioner controls the position of the stabilization device M with respect to the frame by choosing the serrations of the frame to which said device will be attached. By consequence, the user controls and selects the area of the immobilized body part which will be stabilized by the stabilization means M. Said area corresponds to the projection, on the immobilized body part, of the positioning means 327 in the translation direction T-T. The user also controls the position of the positioning means 327 with respect to the adjustment means 340 by choosing one hook like attachment means 351 for attaching the adjustment means 340 to the stabilization device M. Consequently, the user ensures that the positioning means 327 will be in contact with the selected area of the immobilized body part and/or bitten by the mouth of the patient if the head is immobilized.

In a preferred embodiment, the stabilization device N designed for the nose is dismountably fixed on the frame 321 of the stabilization means support. Said stabilization device N comprises fastening means 363, 355, 356 for fastening the stabilization means to said frame 321. In a preferred embodiment, the stabilization device N comprises at least one positioning means 360 suitable to be in contact with an area of the immobilized patient body part and adjustment means 362, 364 for changing the position of the positioning means 360, thereby adapting its position to the targeted area of the immobilized body part.

In the embodiment shown in FIG. 32 and FIG. 33, the positioning means 360 is suitable to be in contact with the nose of the patient. Preferably said positioning means is suitable to be in contact with the nose bone of the patient. Consequently, optimized and/or complete immobilization of the patient's head during treatment in ensured. The positioning means 360 can be made of silicone, rubber, polypropylene or any other suitable material. The positioning means 360 is suitable to be replaced by a new positioning means when required. It is to be understood that the positioning means can be of any other shape and/or any other material.

In a preferred embodiment, the fastening means are components of an actuated lever clamp comprising a lever 363 and at least two clamping jaws 355, 356. The lever 363 is movable between a locked position and an unlocked position. In the locked position, the clamping jaws 355, 356 are at least partially surrounding the edges of the frame 321 and are clamped around said edges thereby fixing the stabilization device to the stabilization means support. In the unlocked position, the clamping jaws 355, 356 are not surrounding the edges of the frame 321 thereby removing the stabilization device from the stabilization means support. Preferably, said clamping jaws 355, 356 are designed to form-fit the serrations 322 of the frame 321. Hence, the user controls the position of the stabilization device N on the frame and thereby the position of the stabilization device with respect to the immobilized body part.

Figure 34:
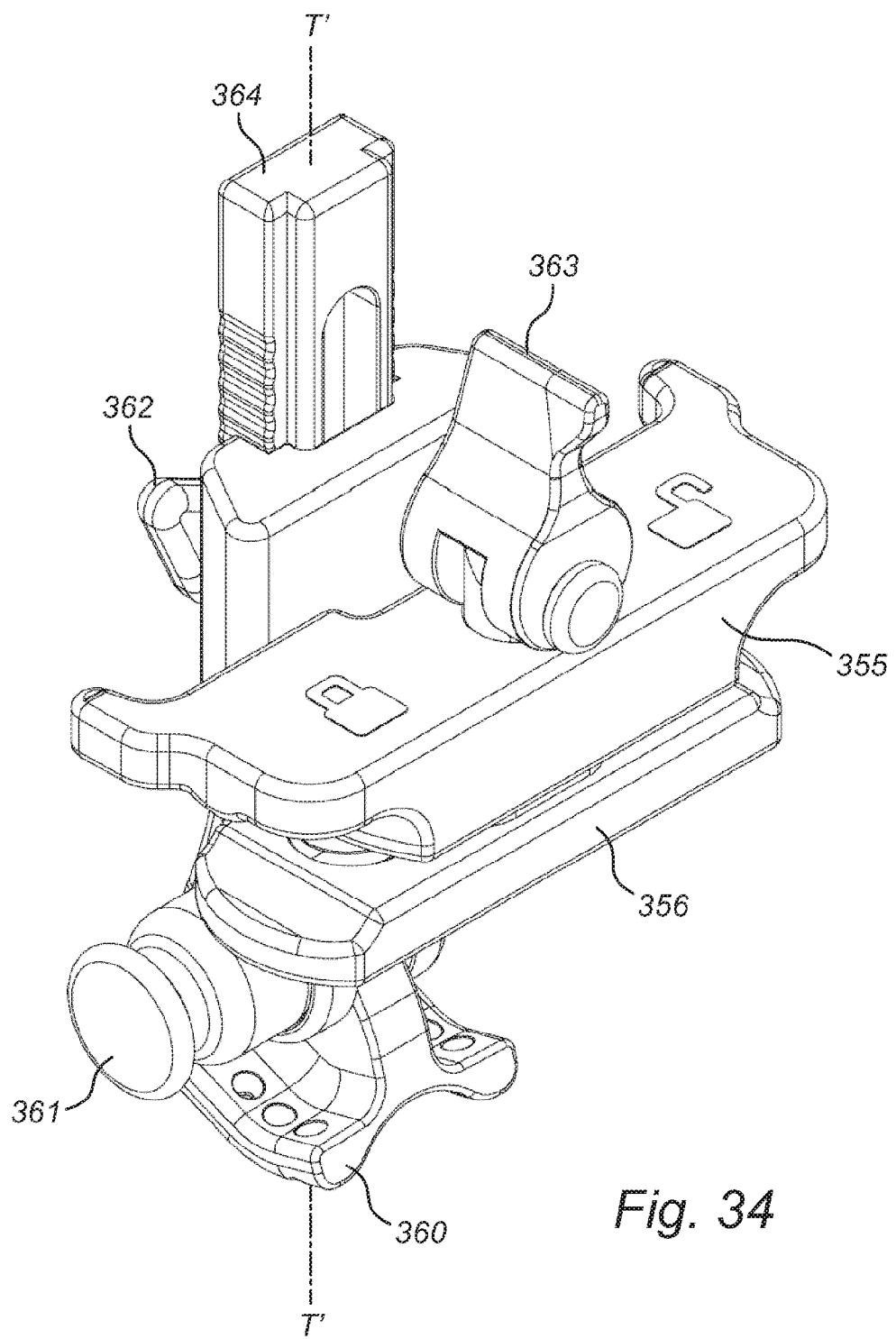
FIG. 34 shows a perspective view of the second stabilization device.

In a preferred embodiment, the positioning means 360 is slidably connected to an adjustment means 364 via at least one blocking means 362. The positioning means 360 is slidable with respect to the adjustment means 364 along a translation axis T'-T' (FIG. 34). Said blocking means is movable between an unblocked position in which the positioning means 360 is slidable with respect to the adjustment means 364 and a blocked position in which the positioning means 360 is not slidable with respect to the adjustment means 364. Consequently user controls the position of the positioning means 360 with respect to the adjustment means 364 (FIG. 34 and FIG. 35).

Figure 35:
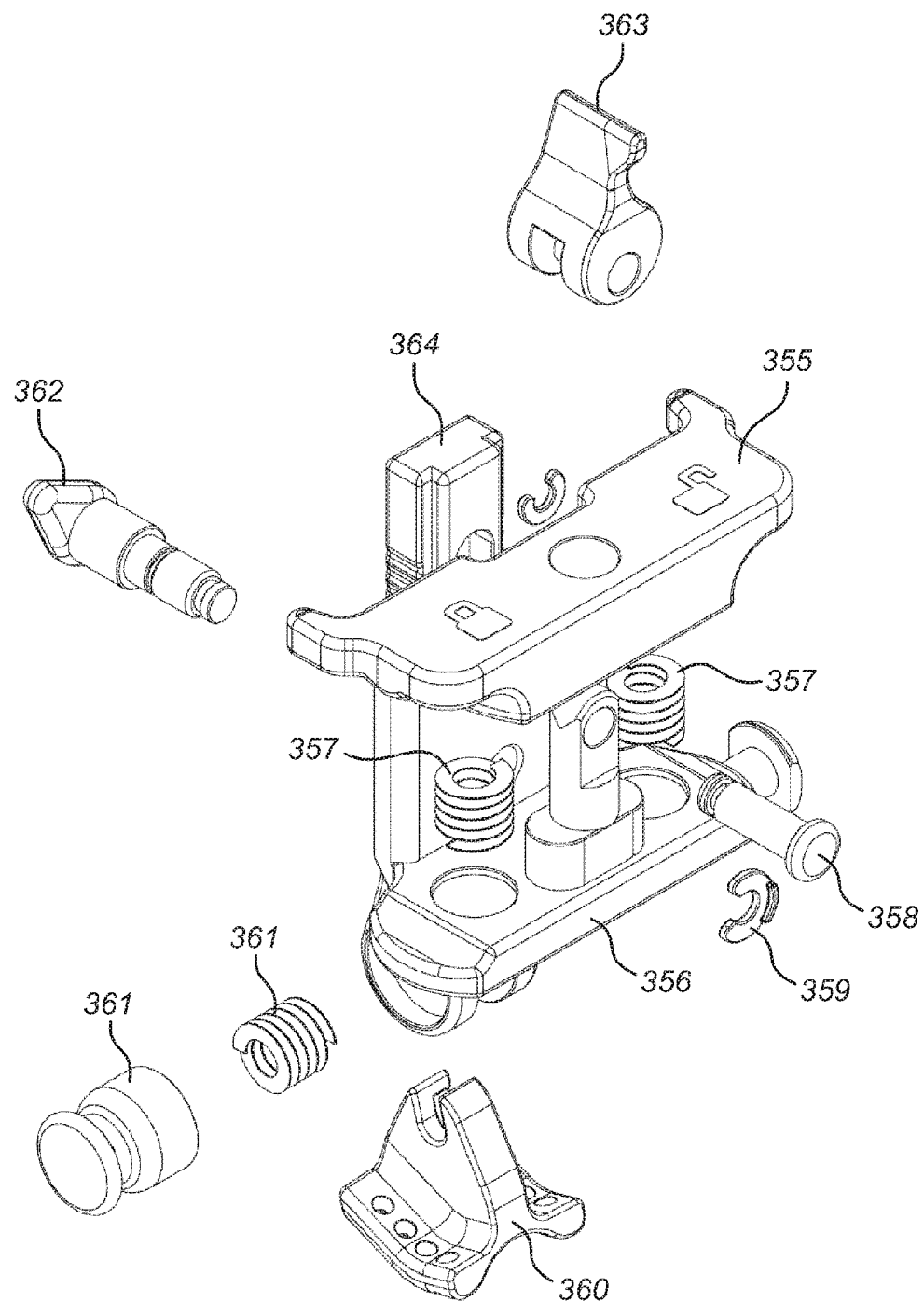
FIG. 35 shows an exploded view of the second stabilization device.

The exploded view of the stabilization device N provided in FIG. 35 shows the different components of the fastening means, i.e. the lever 363 the clamping jaws 355, 356. The same figure further shows the positioning means 360, the adjustment means 364, the blocking means 362 and the different means 357, 358, 359, 361, 361 used for assembling said components. Said means are selected from the group comprising screws, blind, rivets, tacks, nails, nuts, pins, bolts, rivets or any combination thereof. When assembled as shown in FIG. 34, the user can easily select the position of the positioning means 360 with respect to the adjustment means 364 by moving blocking means 362 from the blocked position to the unblocked position and sliding the positioning means 360 with respect to the adjustment means 364 along the translation axis T'-T'.

For attaching the stabilization device N to the frame 321 of the stabilization means support as shown in FIG. 29, the user or practitioner controls the position of the stabilization device N with respect to the frame by choosing the serrations of the frame to which said device will be attached. By consequence, the user controls and selects the area of the immobilized body part which will be stabilized by the stabilization device N. Said area corresponds to the projection, on the immobilized body part, of the positioning means 360 in the translation direction T'-T'. The user also controls the position of the positioning means 360 with respect to the adjustment means 364 by choosing the position of the stabilization device N. Consequently, the user ensures that the positioning means 360 will be in contact with the selected area of the immobilized body part which can be the nose bone if the head is immobilized.

In a fourth aspect, the present invention provides a moldable thermoplastic sheet comprising a circumferential rim 12, 12' which is provided with connection means 8, 8' such as said connection means are corresponding to all or to some attachment means of the device according to an embodiment of the invention. In a preferred embodiment, the connection means 8, 8' are regularly distributed on the circumferential rim 12, 12'.

In a preferred embodiment, the circumferential rim 12, 12' are manufactured from a material having high temperature tolerance. In a further preferred embodiment, the circumferential rim 12, 12' are manufactured from a carbon composite material having low density, more preferably from a carbon composite polymer, most preferably from carbon fiber or carbon fiber reinforced plastics. This is advantageous as the thermoplastic sheets will have a low weight facilitating their used and manipulation by the practitioner.

Figure 6A:
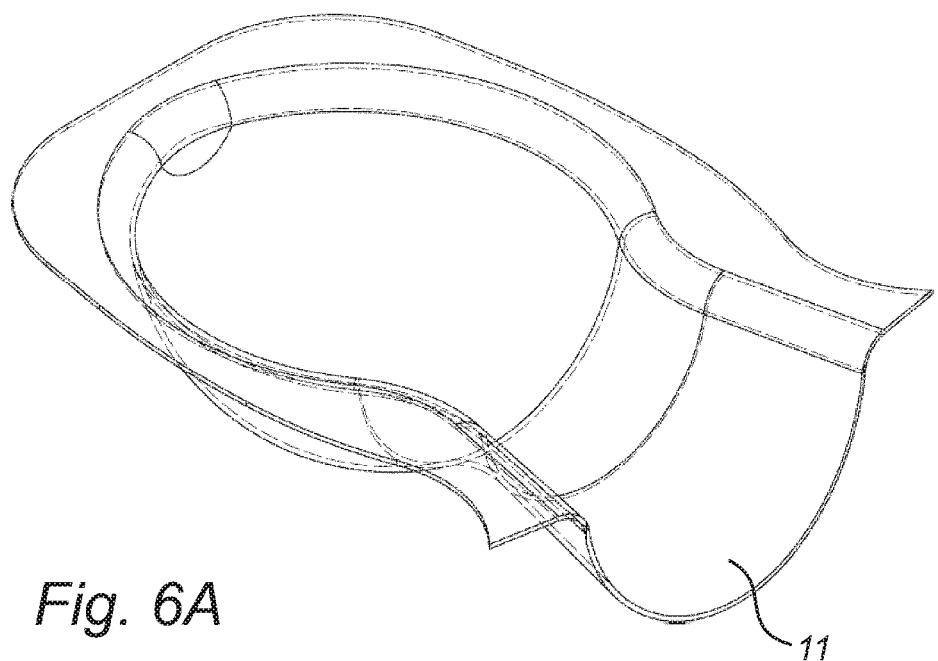
FIG. 6A shows a thermoplastic sheet in final state, after molding and curing. The sheet is devoid of circumferential rim.

FIG. 5 shows an embodiment of a moldable thermoplastic sheet according to the present invention. The moldable thermoplastic sheet is in its initial state and comprises a circumferential rim 12 provided with attachment means 8 and the thermoplastic sheet itself 11. FIG. 6 shows the moldable thermoplastic sheet of FIG. 5 in a final state, i.e. after being heated and molded to conform and cover the anatomical contours of a patient's body portion. Said sheet in its final state might be disconnected from the circumferential rim (FIG. 6A) which for instance allows optimization of the cleaning of the molded sheet thereby optimizing the hygiene of the mask.

Figure 7A:
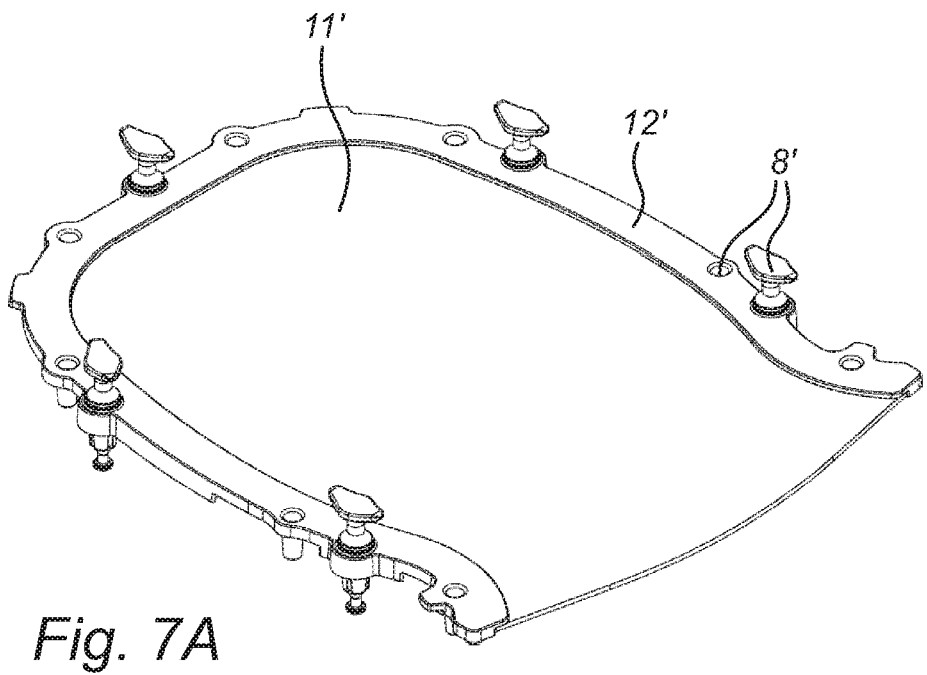
FIG. 7A shows an embodiment of the moldable thermoplastic sheet of FIG. 7 which is devoid of opening.

FIG. 7 shows another moldable thermoplastic sheet 11' according to an embodiment of the present invention. The moldable thermoplastic sheet is in its initial state and comprises a circumferential rim 12' provided with attachment means 8' and the thermoplastic sheet itself 11'. The moldable thermoplastic sheet 11' comprises an opening 13' which can correspond to the nose or to the mouth of the patient's when the sheet is cured. The thermoplastic sheet may be provided with more than one opening. FIG. 7A shows another embodiment of the moldable thermoplastic sheet 11' wherein the sheet is devoid of any opening.

In a preferred embodiment, the thermoplastic sheet 11, 11' and the circumferential rim 12, 12' are physically (i.e. heat bonding), mechanically (i.e. clamping) or chemically bonded (i.e. glued). In another preferred embodiment, the thermoplastic sheet 11, 11' and the circumferential rim 12, 12' are dismountably fixed to each other, via snap-fit system for instance.

In a preferred embodiment, the circumferential rim 12, 12' comprises at least one recess 14, 14' in FIG. 2 provided over at least a part of the circumferential rim, said recess 14, 14' is adapted for matingly fixing the circumferential rim to a flanged support member 3 of the device of the present invention described above. In a preferred embodiment, the flanged support member 3 of the device according to the present invention is adapted to snap fit into the recess 14, 14' of the circumferential rim 12, 12' of the moldable thermoplastic sheet 11, 11'.

In a further preferred embodiment, for fixing two moldable thermoplastic sheets 11 and 11' to a flanged support member 3 of the device according to the present invention, the recesses 14 and 14' of the circumferential rims 12 and 12' can be provided such as each recess snap fits an edge (10 or 10' in FIG. 1) of the flanged support member 3.

In a preferred embodiment, the sheets have different elasticity. Preferably, the elasticity ratio of the sheet with the highest elasticity to the sheet with the lowest elasticity is at least 5. In a further preferred embodiment, the elasticity of the less elastic sheet is at least 50%, preferably at least 60%, more preferably at least 65%, most preferably at least 70%. The elasticity of the less elastic sheet is at most 150%, preferably at most 120%, more preferably at most 100%, most preferably at most 80%. Preferably the less elastic sheet is the first sheet, i.e. used for covering a first area of the body part to be immobilized.

The moldable thermoplastic sheets of the invention can be of any composition known to the person skilled in the art and/or described in the prior art and/or available on the market. The thermoplastic sheet can be a single sheet or a laminate which is perforated or non-perforated. The laminate can comprise one or more core thermoplastic layers bound to a support which comprises a mesh and/or a layer of cotton and/or a layer of elastic cotton and/or open cell foam and/or silicone and/or any other soft fabric for providing a comfortable feeling to the patient. The perforations diameter is comprised between 0.1 mm and 3 mm and preferably between 0.5 and 2 mm, more preferably between 1 to 1.3 mm. Said perforations may be positioned in rows separated by 1 mm to 5 mm. The perforations may represent 10% to 90%, preferably 20% to 80%, more preferably 30% to 70% of the sheet surface. The perforations allow the skin of the patient to breathe even after application of the thermoplastic sheets.

In a preferred embodiment, the thickness of the less elastic sheet in its initial state is of from 1.5 to 1.8 mm, preferably about 1.7 mm. The thickness sheet with the highest elasticity, in its initial state, is of from 2 to 2.5 mm, preferably about 2.3 mm. The thickness of the sheet in its initial state is also called pre-molding thickness. The thickness of the sheet in its final state is also called post-molding thickness.

In a preferred embodiment, in their final state, so after being molded and cured, the thickness of the less elastic and the thickness of the sheet having the highest elasticity are very close to each other and preferably equal to each other. The post molding thickness is of from 1.4 to 1.9 mm, preferably of from 1.5 to 1.8 mm. The equal post molding thickness of the sheets is advantageous as it provides for a uniform radiation level independently from the position at which said radiations are applied. This means that the inhibition of the radiation by the sheets will be uniform through the double shell mask.

In a preferred embodiment, the thermoplastic sheet shows reduced draping when warmed. Gamma irradiation can be applied or can be not applied to the thermoplastic sheet of the invention. The thermoplastic sheet can be coated or non-coated. A polyurethane polymer coating can be applied on the thermoplastic sheet.

In a preferred embodiment, the thermoplastic sheet is optically transparent. The optical transparency permits using positioning markers on one or both of the immobilization device and the body part to facilitate re-positioning. This renders the thermoplastic sheet suitable for use in radiation therapy and diagnostic imaging and any other applications where an accurate re-positioning of the immobilization device is of high importance.

In another preferred embodiment, the thermoplastic sheet of the present invention has a softening temperature of less than 60° C., preferably of less than 65° C. and comprises a thermoplastic copolymer of a lactone and a lactide in a weight ratio of from 96:4 to 87:13, respectively, wherein the copolymer has a melt temperature Tm in the range of from 47 to 58° C.

In a preferred embodiment, said copolymer of the thermoplastic sheet has a melt temperature Tm in the range of from 50 to 85° C., preferably from 65 to 75° C. and a crystallisation temperature Tc in the range of from 19 to 25° C.

In a preferred embodiment, the copolymer of the thermoplastic sheet has a molecular weight of at least 30000, and preferably from 40000 to 100000.

In another preferred embodiment, the copolymer of the thermoplastic sheet is obtained from a lactone and lactide in a weight ratio of from 93:7 to 91:9.

In another preferred embodiment, the thermoplastic sheet of the present invention comprises a core layer having an upper surface and lower surface. The core layer has a thermoplastic composition comprising polycaprolactone and polyurethane. The thermoplastic sheet comprises also a first outer layer disposed over the upper surface of the core layer and a second outer layer disposed over the lower surface of the core layer. In a preferred embodiment, the first outer layer comprises a material formed from a yarn comprising polyamide and elastane. In a preferred embodiment, the second outer layer comprises open cell foam. The first and the second outer layers are bonded to the core layer so as to form a single sheet.

In a preferred embodiment, the core layer comprises 20% to 40%, polyurethane, and 60% to 80% (w/w) polycaprolactone.

In a preferred embodiment, the core layer further comprises between 1 to 40% (w/w) of non-metallic, heat-accumulating microspheres.

In a preferred embodiment, the yarn of the first outer layer comprises between 80% to 95% polyamide, and between 5% and 15% elastane. The thickness of the first outer layer is between 0.05 and 1.5 mm. The fabric weight of the first outer layer is between 210 $g/m^2$ and 230 $g/m^2$.

In a preferred embodiment, the second outer layer is made from polyurethane, polyester polyurethane or polyether open-cell foam.

In a preferred embodiment, the thermoplastic sheet comprises an intervening layer disposed between the core layer and the first outer layer, and/or disposed between the core layer and the second outer layer, made from the same material as the core and with higher polycaprolactone content.

In a preferred embodiment, the thermoplastic sheet has a maximum total thickness of 1.5 to 1.7 mm.

In another preferred embodiment, the thermoplastic sheet of the present invention is as described in JP 2 527 348 and comprises a mixture of a polycaprolactone resin with a styrene/acrylonitrile copolymer resin. Preferably, the caprolactone monomer is reacted at 100-230° C. in the presence of a catalyst by using water in the monomer as an initiator to obtain a polycaprolactone resin (A) of a relative viscosity (measured with a capillary viscometer) of 1.50-2.80. Separately, a styrene monomer is copolymerized with 20-35 wt % acrylonitrile monomer to obtain a styrene/acrylonitrile copolymer resin (B). Component A is mixed with component B at a weight ratio of 50-95/50-5, and the resulting mixture is optionally mixed with a metal salt of a higher fatty acid (e.g., calcium stearate).

In a preferred embodiment, when cured, the thermoplastic sheet of the invention shows limited shrinking and is soft such as to provide comfort to the patient.

In a preferred embodiment, the thermoplastic sheet is directly moldable on the human body and presents the advantage that it is unbreakable in case of hard handling or after falling. Moreover, the thermoplastic sheet is optically transparent which gives the possibility to observe whether or not it has been properly molded to the body part. The thermoplastic sheet can also be semi-transparent or opaque.

In another preferred embodiment, the invention provides for the immobilization of a body part wherein the sheets are pre-formed. A pre-formed sheet is herein called cast. Preferably, casts are 3D printed casts that conform and cover the body part to be immobilized. The casts are suitable to be connected and retained by a device comprising at least one flanged support member which is suitable to be mounted to a fixation surface. Preferably, two casts are provided wherein a first cast is designed to conform the anatomical contours of a first area of the body part and a second cast is designed to conform the anatomical contours of a second area of the body part thereby forming a double shell mask enclosing said body part. The body part is thereby immobilized free from the fixation surface by the casts and the device.

In a preferred embodiment, the casts are produced using any tool or system known to the person skilled in the art. Preferably said casts are printed according to the patient's body part to be immobilized.

Figure 36:
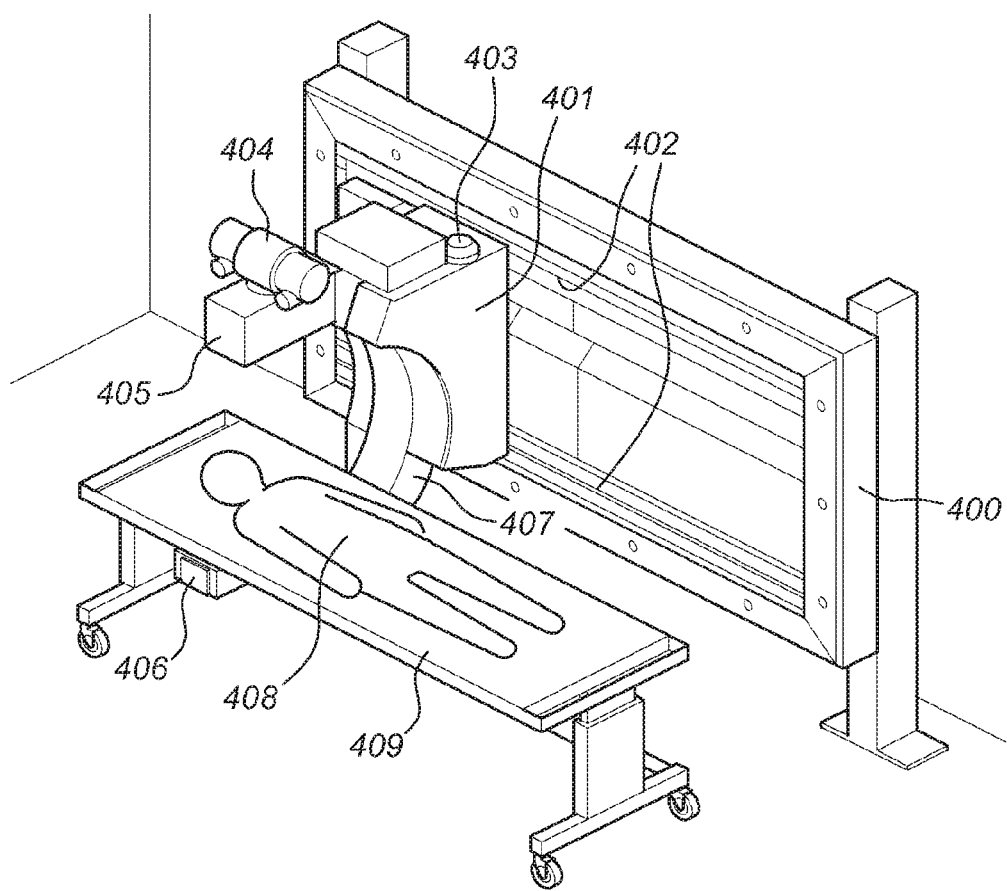
FIG. 36 shows an embodiment of the invention wherein the body part is scanned for forming the sheets.
Figure 37:
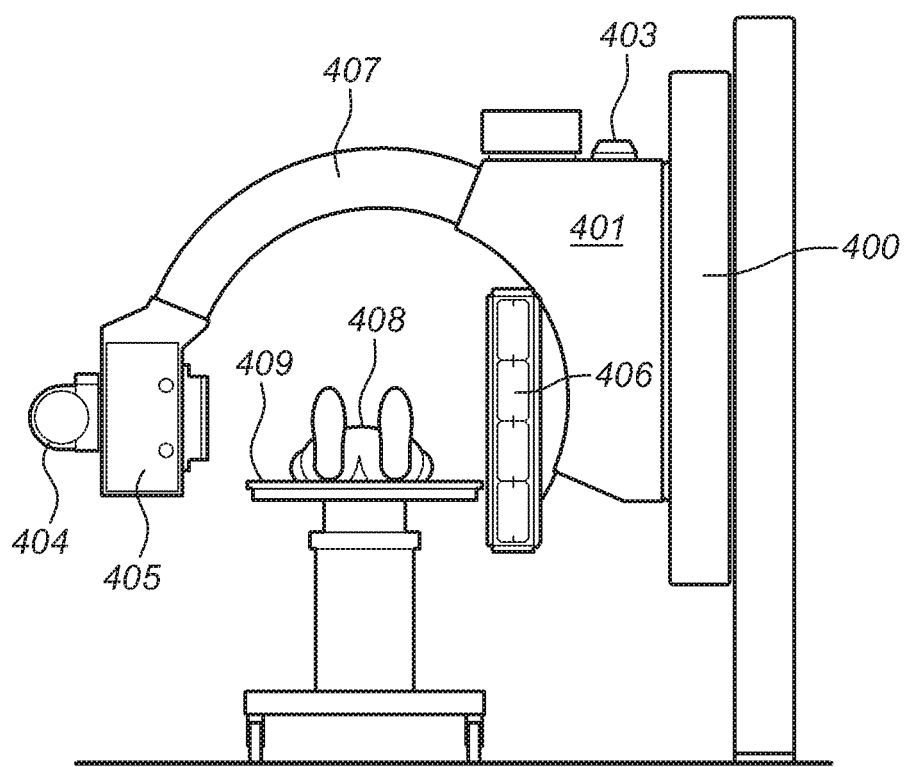
FIG. 37 shows a side view of the embodiment of FIG. 36.

FIG. 36 and FIG. 37 show an embodiment of the system of the invention wherein the body part to be immobilized is scanned and the casts printed using a 3D printer. The system comprises a frame 400 mounted on a wall or another fixed structure defines a pair of rails 402 with which a motorised drive mechanism 403 engages to drive an arm 407 linearly back and forth in a first, axial direction of movement. Said axial direction is preferably parallel to the longitudinal direction of a table 409 on which a patient 408 is placed for scanning the body part to be immobilized. Said axial direction corresponds preferably to the direction of scanning in use. The drive mechanism 403 further comprises a housing 401 in which the arm 407 is movable by the drive mechanism 403 thereby allowing a 3D imaging and/or scanning apparatus 404 of the system to rotate about an axis parallel with the axial scanning direction. This rotation allows the imaging and/or scanning of the patient's body part over 360°.

Figure 38:
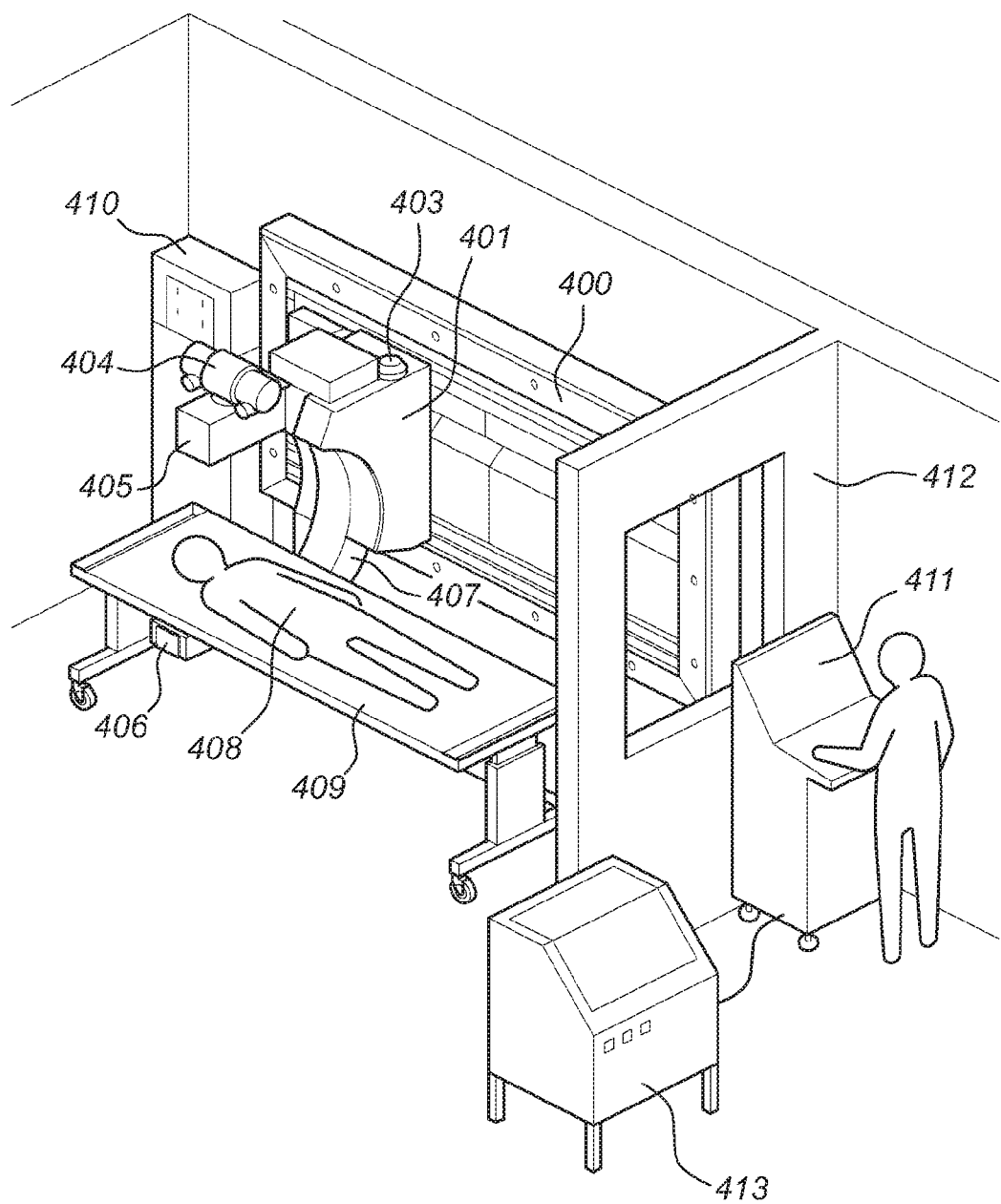
FIG. 38 shows the embodiment of FIG. 36 and an embodiment of controlling the formation of the sheets.

The 3D imaging or scanning apparatus 404 for obtaining a 3D image or scan of said patient's 408 body part is preferably provided on a head 405 connected to the housing 401 and/or the arm 407. The head 405 and thereby the 3D imaging or scanning apparatus 404 are movable by the movement of the arm 407. The 3D imaging or scanning apparatus may also comprise a scanning unit or detector for visualising internal structures such as bone structures, such as e.g. a seismographic 3D scanner. The system might be further provided with a detector unit 406. Preferably said unit 406 and the head 405 are supported at opposite ends of the curved arm 407. The detector unit 406 transmits the data acquired by said 3D imaging apparatus to an acquisition unit 411, such as a computer, for acquiring the data collected by the 3D imaging or scanning apparatus 404 and for processing said obtained data to obtain a model for two 3D casts 611 (FIG. 38). Preferably, said acquisition unit 411 is operated by a qualified operator. After processing the data collected by the 3D imaging or scanning apparatus 404 in the acquisition unit 411, instruction is send to the 3D printing device 413 (FIG. 38) for printing the casts which are conforming the anatomical contours of the scanned body part.

The collected data comprises parameters selected by the operator. Said parameters comprise the length, the width, the muscle content, the fat content of the body part to be immobilized or any combination thereof. After processing the data in the acquisition unit, the operator can choose the material of the casts which is most appropriate for the immobilization of the body part. Said casts can be made from a material selected from the group comprising rigid-elastic material, plastics, polyethylene, polypropylene, polyvinylchloride, polystyrene, polyethylene terephthalate, polycarbonate or any combination thereof.

Figure 39A:
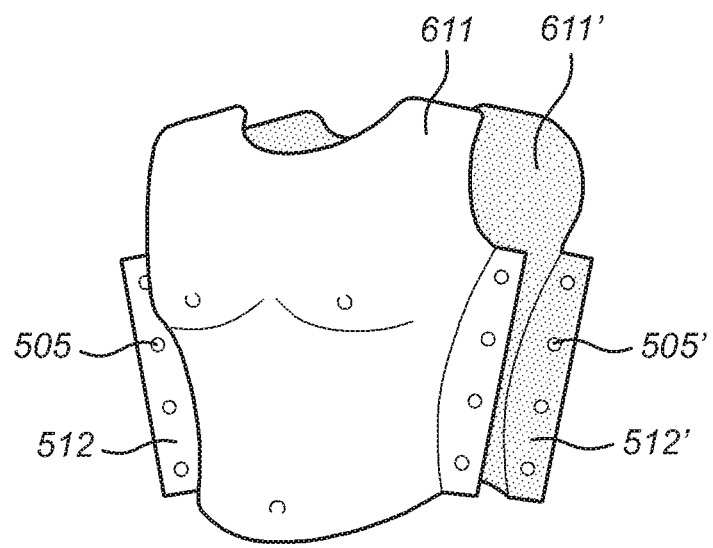
FIG. 39A shows an embodiment of the formed sheets designed for immobilizing the trunk of a patient.
Figure 39B:
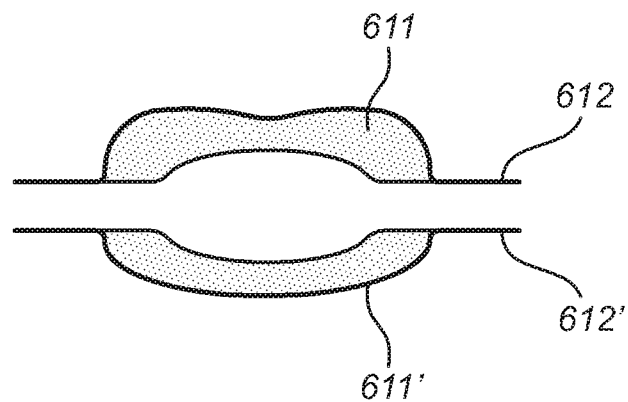
FIG. 39B shows side view of FIG. 39A.

FIG. 39A provides a schematic view of two 3D casts 611, 611' used for enclosing the trunk of a patient. Preferably, each 3D printed cast is provided with a side rim 512, 512' suitable to be connected and fixed to a flanged support member as described above. Each rim is preferably provided with a plurality of connection means 505, 505'. FIG. 39B provides a side view of the 3D printed casts of FIG. 39A. By connecting the 3D printed casts 611, 611' to a flanged support member as described above and according to the invention, said casts will conform the anatomical contours of the patient's body part. The rim 512, 512' can also be 3D printed thereby perfectly matching the connection means of the rim to the attachment means of the flanged support member 503.

The present invention hence provides a system for immobilization of a patient body part, comprising: —a device comprising a flanged support member as described above and adapted to receive at least two casts; —a first casts 611; and —a second casts 611' whereby the system is adapted for supporting the immobilized body part free from the fixation surface by the two casts and the device.

The current invention further provides a method for producing pre-formed sheets, also called, casts for immobilization of a patient's body part comprising the steps of:

scanning said patient's body part with a 3D scanner, thereby obtaining scan data of said body part;

collecting said scan data of said body part;

processing the collected scan data of said body part thereby obtaining a model which is fitting and personalized to the scanned body part;

producing casts which are suitable to be attached and fixed to a flanged support member thereby supporting the immobilized body part free from the fixation surface by the two casts and the device. Preferably, the casts are produced by 3D printing said model in two 3D printed casts that, when attached and fixed to the flanged support member are conform to the anatomical contours of said patient's body part.

Figure 40:
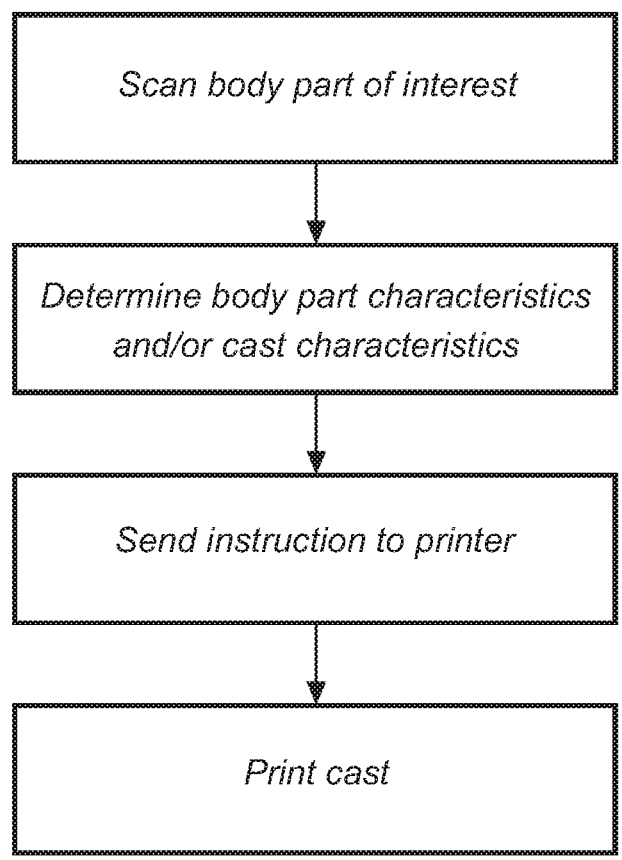
FIG. 40 shows a flow chart of an embodiment of a method for making pre-formed sheets according to present invention.

FIG. 40 provides a flow chart of a method for making said casts. The method comprises the steps of (i) scanning the body parts of interest; (ii) determining body part characteristics for instance by the acquisition unit; (iii) sending instructions to a 3D printer; and (iv) obtaining said pre-formed 3D printed casts.

The further provides a method for immobilization of a patient body part for radiotherapy applications comprising the steps of:

scanning said patient's body part with a 3D scanner, thereby obtaining scan data of said body part;

collecting said scan data of said body part;

processing the collected scan data of said body part thereby obtaining a model which is fitting and personalized to the scanned body part;

producing at least two casts, mounting a device comprising a flanged support member to a fixation surface; said flanged support member is adapted to receive and retain at least the two casts;

mounting a first cast to the flanged support member;

placing the patient body part to be immobilized on said first cast thereby covering the anatomical contours of a first area of said body part; and mounting a second cast to the flanged support member thereby covering the anatomical contours of a second area of said body part which is not covered by the first cast, wherein the method is adapted for supporting the immobilized body part free from the fixation surface by the two casts and the device.

Figure 41:
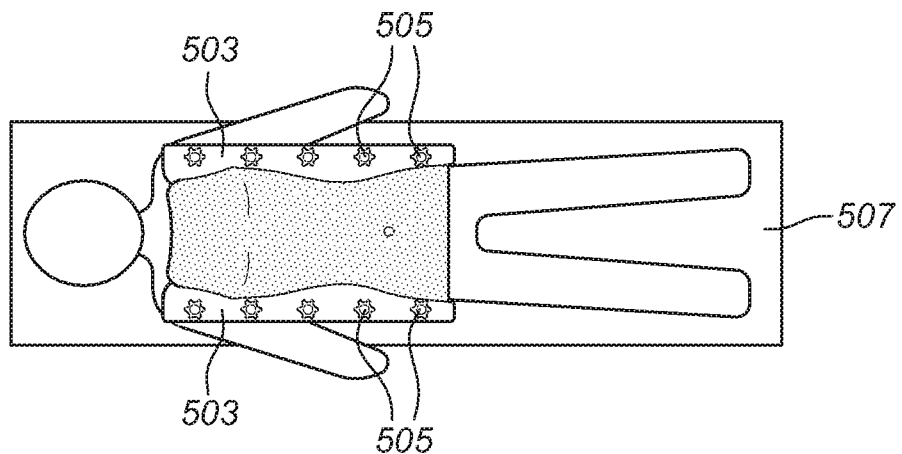
FIG. 41 shows a top view of an immobilized trunk of a patient.
Figure 42:
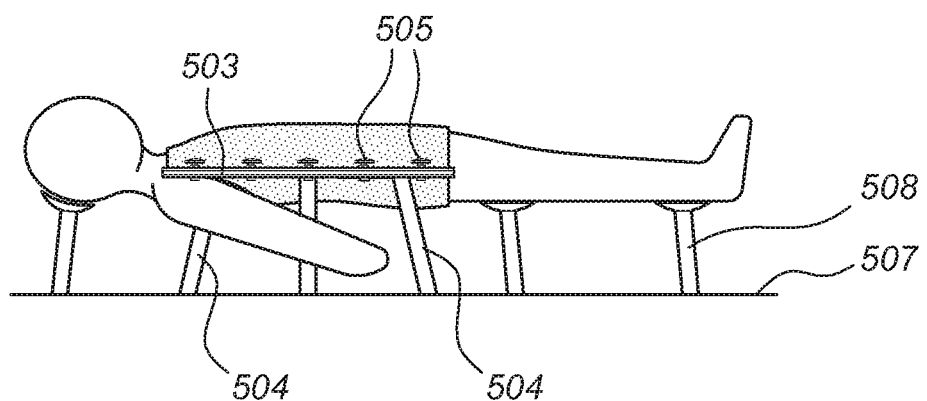
FIG. 42 shows a side view of the immobilized trunk of a patient shown in FIG. 42.

FIG. 41 and FIG. 42 show the pre-formed 3D printed casts in use for immobilization of the patient's trunk, whereby said trunk is enclosed in two 3D printed casts. Said 3D printed casts are mounted on a flanged support member 503 which is mounted and fixed to a fixation surface 507 using a plurality of upstanding circumferential support legs 504. The fixation surface in this embodiment might be a carbon fiber surface or any surface made from any suitable material. The remaining body part of the patient might be supported with any other material for providing comfort to the patient during treatment. For instance, in FIG. 42, further support means 508 are used for positioning other body parts of the patient, in order to provide comfort to said patient and to further improve an accurate positioning of the various organs. It is to be understood that any other support means known to the person skilled in the art might be used.

The system and the method according to an embodiment of the invention wherein the body part to be immobilized is scanned for producing casts are advantageous. Said system and method provide for personalized casts which might be adapted to any variation of the body part—weight gain or loss. Furthermore, the casts material is selected according to the patient's specific body composition—fat, muscles. In addition the immobilized part is free from the fixation surface and is only supported by the device and the casts thereby presenting the advantages as described above.

Preferably, the sheet according to any embodiment of the invention—moldable thermoplastic sheet or any other pre-formed sheet or cast—is treated with an antibacterial product before being used. In a further preferred embodiment, said sheet comprises at least one antibacterial compound or a mixture of antibacterial compounds. Further, the sheet is not susceptible to any crimping during use or storage.

The device according to any embodiment of the present invention is suitable to be used in the system according to any embodiment of the present invention. Further, in the method according to any embodiment of the present invention, the system and/or the device as provided by the invention are suitable to be used.

It is to be understood that the features described for an embodiment of the present invention are suitable to be applied to any other described embodiment of the invention without departing from the scope of this invention which is defined by the appended claims.

Although the present invention has been described with reference to preferred embodiments thereof, many modifications and alternations may be made by a person having ordinary skill in the art without departing from the scope of this invention which is defined by the appended claims.

What is claimed is:

1. A system for immobilization of a patient body part for radiotherapy applications comprising:
   a device comprising at least one flanged support member which is suitable to be mounted to a fixation surface and is adapted to receive and retain at least two sheets,
   a first sheet for covering the anatomical contours of a first area of said body part, and
   a second sheet for covering the anatomical contours of a second area of said body part which is not covered by the first sheet, wherein said first sheet and said second sheet each comprise a single circumferential rim which is provided with connection means for mounting said sheets to the flanged support member, and wherein each of said circumferential rims are dismountably fixed to the thermoplastic sheets,
   and wherein the flanged support member and the circumferential rims have a U shape, and are at least partially superimposable, whereby the system is adapted for supporting the immobilized body part free from the fixation surface by the two sheets and the device.

2. The system according to claim 1, wherein the first sheet is designed to conform to the anatomical contours of the first area of the body part and the second sheet is designed to conform to the anatomical contours of the second area of the body part thereby forming a double shell mask enclosing said body part.

3. The system according to claim 1, comprising at least one support member fixation means for mounting the flanged support member of the device to the fixation surface at a distance from said fixation surface, thereby mounting the flanged support member substantially parallel to the fixation surface.

4. The system according to claim 1, wherein the flanged support member is provided with a plurality of attachment means adapted to receive and retain the sheets.

5. The system according to claim 1, wherein the connection means of the circumferential rim of the sheet are positioned such as to correspond to the connection means of the circumferential rim of the second sheet and/or to the attachment means of the flanged support member of the device.

6. The system according to claim 1, comprising at least one stabilization means suitable to be dismountably fixed to the flanged support member for optimizing the immobilization of said body part.

7. A method for immobilization of a patient body part for radiotherapy applications comprising the steps of:
   mounting a device comprising a flanged support member to a fixation surface, wherein said flanged support member has a U shape and is adapted to receive and retain at least two sheets;
   mounting a first sheet to the flanged support member, wherein said first sheet comprises a U shape circumferential rim which is provided with connection means for mounting the sheet to the flanged support member;
   placing the patient body part to be immobilized on said first sheet thereby covering the anatomical contours of a first area of said body part; and
   mounting a second sheet to the flanged support member thereby covering the anatomical contours of a second area of said body part which is not covered by the first sheet,
wherein said second sheet comprises a U shape circumferential rim which is provided with connection means for mounting the sheet to the flanged support member and wherein each of said circumferential rims are dismountably fixed to the thermoplastic sheets,
and wherein the method is adapted for supporting the immobilized body part free from the fixation surface by the two sheets and the device.

8. The method according to claim 7, wherein the first and the second sheets are suitable to be formed on the patient body part such as to conform to the anatomical contours of said patient body part.

9. The method according to claim 7, wherein the first and the second sheets are pre-formed sheets which conform to the anatomical contours of the patient body part.

10. The method according to claim 7, comprising the step of scanning the body part for pre-forming the first and the second sheets.

* * * * *